(12) United States Patent
Van Noy et al.

(10) Patent No.: US 12,390,365 B2
(45) Date of Patent: *Aug. 19, 2025

(54) INTRAOCULAR LENS INJECTOR

(71) Applicant: ALCON INC., Fribourg (CH)

(72) Inventors: Stephen J. Van Noy, Southlake, TX (US); David Anthony Downer, Fort Worth, TX (US); Kyle Brown, Fort Worth, TX (US); Yinghui Wu, Cedar Hill, TX (US)

(73) Assignee: ALCON INC., Fribourg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/859,793

(22) Filed: Jul. 7, 2022

(65) Prior Publication Data

US 2022/0339031 A1 Oct. 27, 2022

Related U.S. Application Data

(63) Continuation of application No. 16/744,646, filed on Jan. 16, 2020, now Pat. No. 11,413,187, which is a continuation of application No. 15/049,315, filed on Feb. 22, 2016, now Pat. No. 10,588,780.

(60) Provisional application No. 62/208,064, filed on Aug. 21, 2015, provisional application No. 62/128,356, filed on Mar. 4, 2015.

(51) Int. Cl.
*A61F 2/16* (2006.01)
*A61F 9/007* (2006.01)

(52) U.S. Cl.
CPC .............................. *A61F 9/00736* (2013.01)

(58) Field of Classification Search
CPC ...... A61F 2/1662; A61F 2/167; A61F 2/1664; A61F 2/1667; A61F 2/1672; A61F 9/0017; A61F 2/1678; A61F 2/1675; A61F 9/00736; A61F 9/00745; A61F 9/00754; A61F 9/00763
See application file for complete search history.

(56) References Cited

U.S. PATENT DOCUMENTS

| 5,873,879 | A | * | 2/1999 | Figueroa | A61F 2/1691 |
| | | | | | 606/107 |
| 6,001,107 | A | * | 12/1999 | Feingold | A61F 2/1664 |
| | | | | | 606/107 |
| 6,010,510 | A | * | 1/2000 | Brown | A61F 2/167 |
| | | | | | 606/107 |

(Continued)

*Primary Examiner* — Majid Jamialahmadi

(57) ABSTRACT

Apparatuses, systems, and methods for implanting an intraocular lens into an eye are described. For example, an intraocular lens injector may include a plunger and an injector body that includes an insertion depth guard and a nozzle extending therefrom. The insertion depth guard is disposed at a distal end of the injector body to limit a distance that the nozzle penetrates the eye. The intraocular lens injector may also include a biasing element configured to generate a counterforce to distal movement of the plunger through the injector rod. An example intraocular lens injector may include a biasing element to produce a counterforce that opposes advancement of the plunger through the injector body. The counterforce provides for a more continuous advancement of the plunger while reducing or substantially eliminating abrupt changes in the rate at which the plunger is advanced through the injector body.

20 Claims, 17 Drawing Sheets

(56) References Cited

U.S. PATENT DOCUMENTS

| | | | | |
|---|---|---|---|---|
| 6,143,001 A * | 11/2000 | Brown | A61F 9/00 | |
| | | | 606/107 | |
| 2003/0040755 A1* | 2/2003 | Meyer | A61F 2/167 | |
| | | | 606/107 | |
| 2005/0149057 A1* | 7/2005 | Rathert | A61F 2/167 | |
| | | | 606/107 | |
| 2007/0270945 A1* | 11/2007 | Kobayashi | A61F 2/1664 | |
| | | | 606/107 | |
| 2009/0036898 A1* | 2/2009 | Ichinohe | A61F 2/1678 | |
| | | | 606/107 | |
| 2009/0292293 A1* | 11/2009 | Bogaert | A61F 2/1664 | |
| | | | 606/107 | |
| 2010/0010452 A1* | 1/2010 | Paques | A61F 9/0017 | |
| | | | 604/218 | |
| 2010/0217273 A1* | 8/2010 | Someya | A61F 2/1678 | |
| | | | 606/107 | |
| 2011/0288557 A1* | 11/2011 | Kudo | A61F 2/1672 | |
| | | | 606/107 | |
| 2015/0066043 A1* | 3/2015 | Nallakrishnan | A61F 2/167 | |
| | | | 606/107 | |

\* cited by examiner

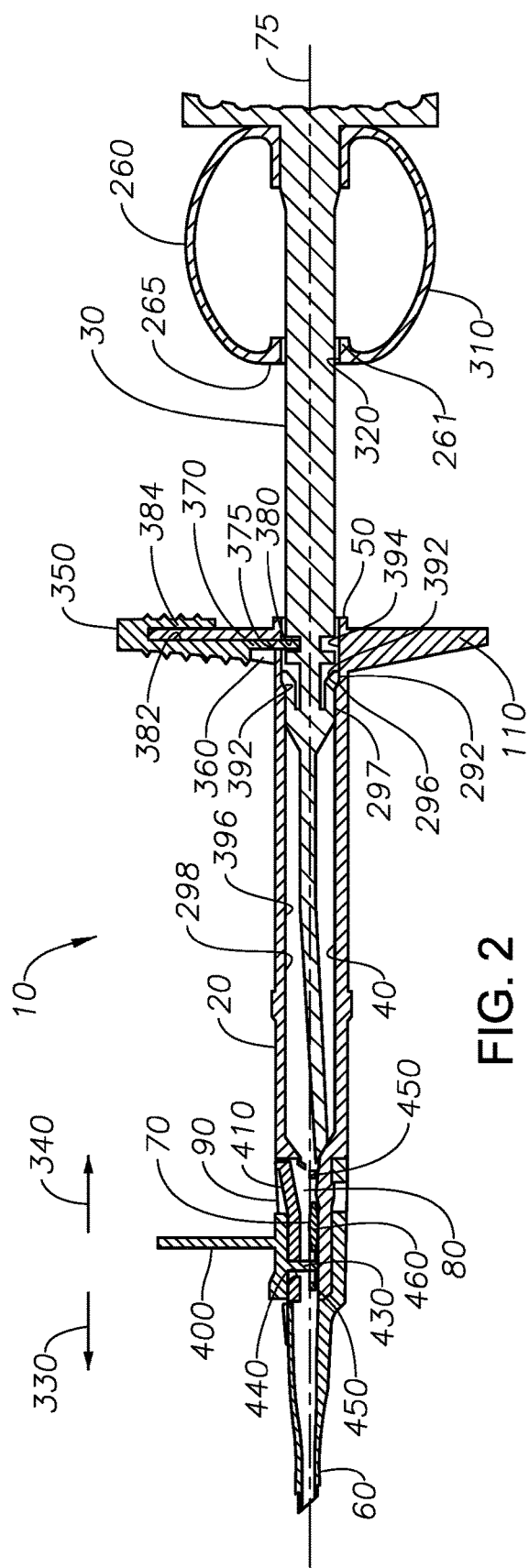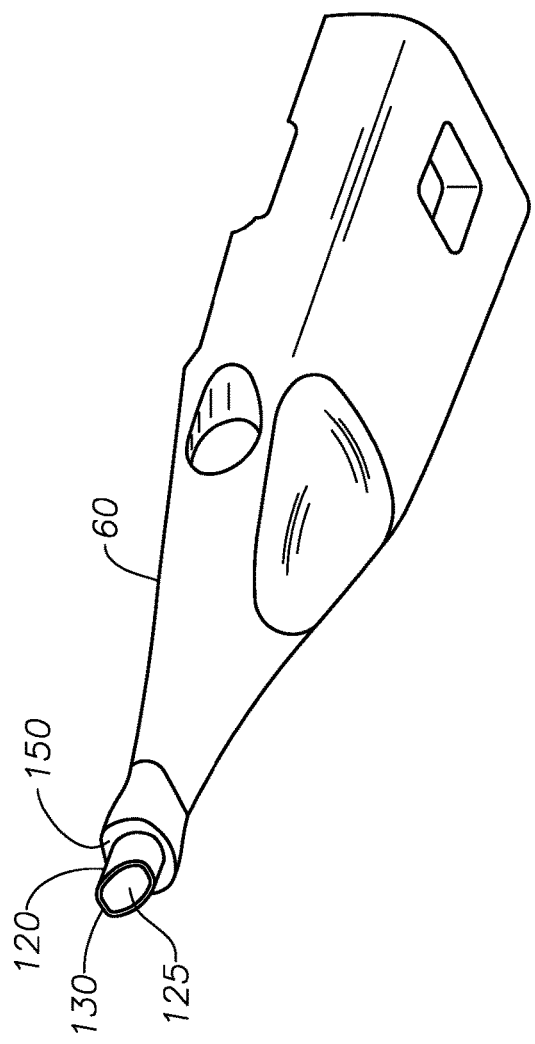
FIG. 2
FIG. 3

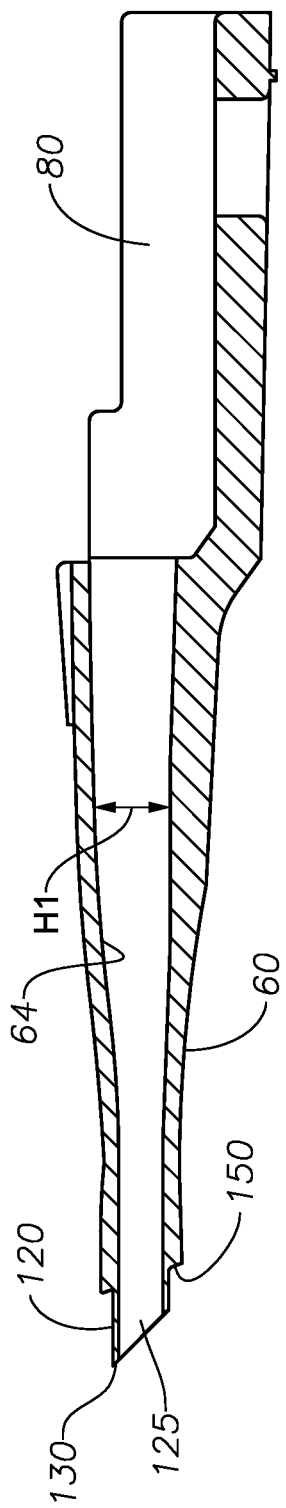
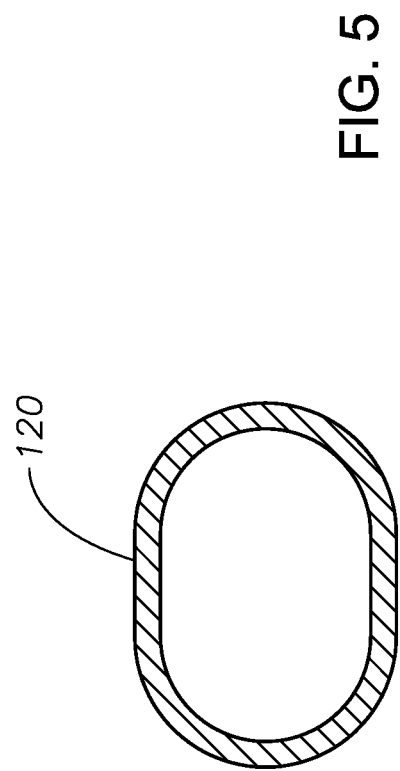
FIG. 4
FIG. 5

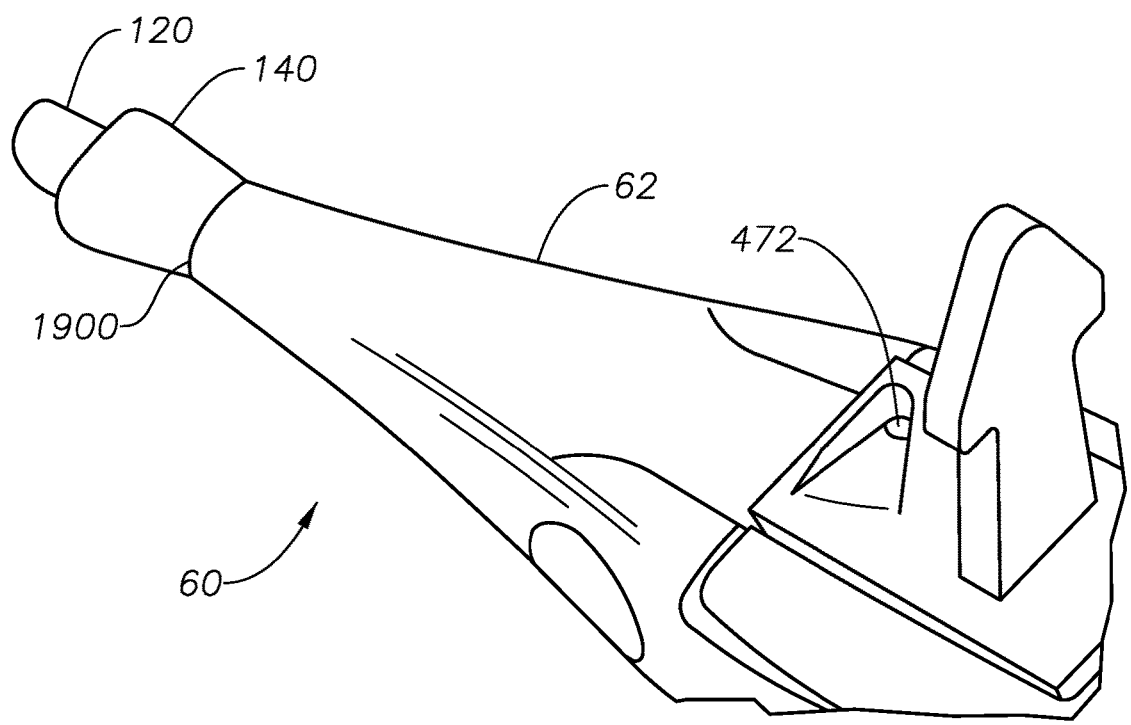
FIG. 19
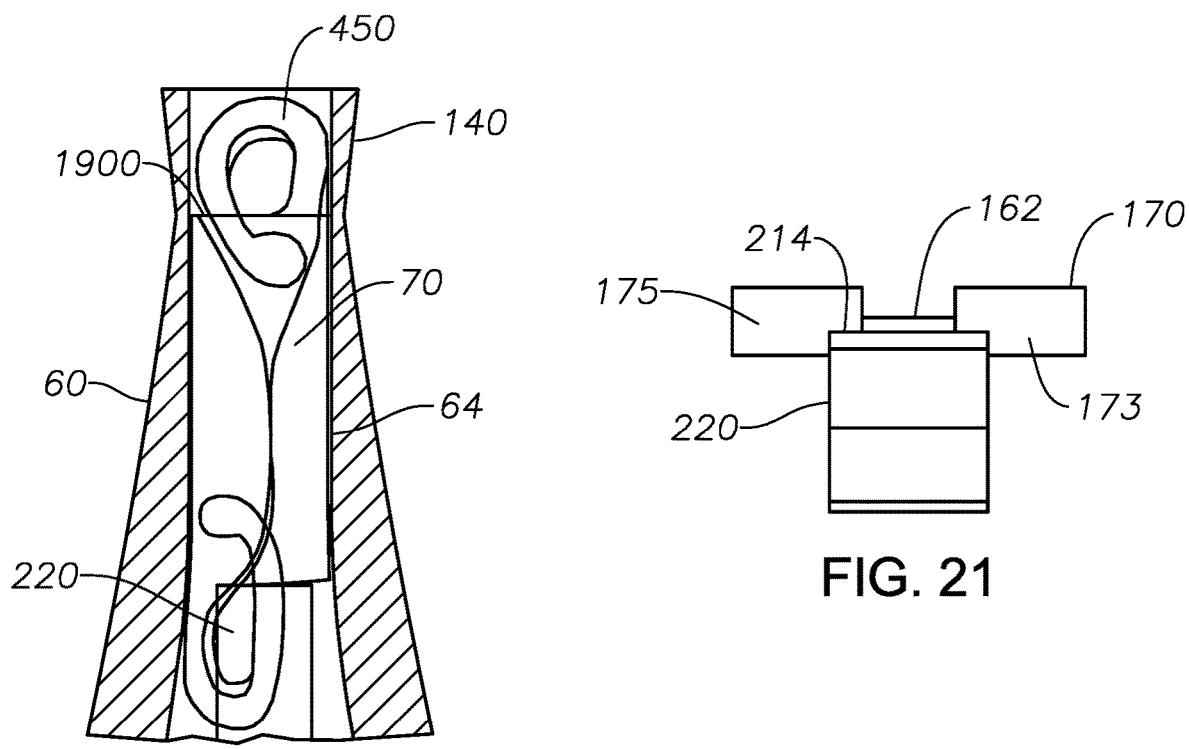
FIG. 20
FIG. 21

INTRAOCULAR LENS INJECTOR

CROSS-REFERENCE TO RELATED APPLICATIONS

This application is a continuation of U.S. application Ser. No. 16/744,646, filed Jan. 16, 2020, and claims the benefit of U.S. application Ser. No. 15/049,315, filed Feb. 22, 2016, and claims the benefit of U.S. Provisional Application No. 62/128,356, filed Mar. 4, 2015, and claims the benefit U.S. Provisional Application No. 62/208,064, filed Aug. 21, 2015, the entire contents of which are included herein by reference.

TECHNICAL FIELD

The present disclosure relates to systems, apparatuses, and methods for intraocular lens injectors.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens. When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial intraocular lens ("IOL").

Many cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. An IOL injector is used to deliver an IOL into the eye.

SUMMARY

According to one aspect, the disclosure describes an intraocular lens injector that may include an injector body, and a plunger slideable within a bore formed in the injector body. The injector body may include the bore, an interior wall defining the bore, an insertion depth guard disposed at a distal end of the injector body, and a nozzle extending distally beyond the insertion depth guard. The insertion depth guard may include a flanged surface.

Another aspect of the disclosure encompasses an intraocular lens injector. The intraocular lens injector may include an injector body and a plunger. The injector body may include a bore defined by an interior wall and a nozzle formed at a distal end of the injector body. The plunger may be slideable in the bore and may include a plunger tip. The tip may include a first groove and a second groove nested within the first groove.

Another aspect of the disclosure encompasses an intraocular lens injector that includes an injector body and a plunger. The injector body includes a bore defined by an interior wall and a nozzle formed at a distal end of the injector body. The plunger is slideable in the bore and includes a plunger tip and a longitudinal axis. The plunger tip includes a first protrusion extending distally from a first side of the plunger tip and a hinge disposed at a proximal end of the first protrusion. The first protrusion extends at an oblique angle relative to the longitudinal axis and pivotable about the hinge.

The various aspects may include one or more of the following features. The flanged surface may be a curved surface. The curved surface may be a spherical surface. The plunger may include a body portion and a biasing element disposed adjacent to a proximal end of the body portion. The biasing element may be deformable upon engagement with the injector body to produce a force resistive to further advancement of the plunger through the bore. The biasing element may include a channel, and wherein the body portion of the plunger may extend through the channel. The injector body may include a tab formed at a proximal end thereof, a groove extending through the tab, and an aperture aligned with the groove. The intraocular lens injector may also include a plunger stop. The plunger stop may include a protrusion. The plunger stop may be removably received in the groove such that the protrusion extends through the aperture and into a slot formed in the plunger. The plunger may include a cantilevered member. The bore may include a shoulder, and the aperture formed in the injector body may align with the slot formed in the plunger when the cantilevered member engages the shoulder.

The various aspects may also include one or more of the following features. The injector body may include a compartment in communication with the bore. The compartment and the bore may be coupled together at an interface. The interior wall may include a tapered portion that defines an opening that provides communication between the bore and the compartment. The interior wall may include a flexible wall portion disposed at the opening. The plunger may include a plunger rod, and the compartment may include a receiving surface adapted to receive an intraocular lens. The receiving surface may include a contoured ramp disposed distally from the opening. The flexible wall portion may be configured to align the plunger rod within the opening. The contoured ramp may be configured to deflect the plunger rod in a second direction opposite the first direction as the plunger rod is advanced through the compartment. The plunger may include a cantilevered member, and the cantilevered member may deflectively engage the interior wall of the bore as the plunger is advanced through the bore.

The various aspects may include one or more of the following features. The second groove may be formed at a first end of the first groove. A second end of the first groove opposite the first end may be configured to capture a trailing haptic of an intraocular lens disposed in the injector body, and the second groove may be adapted to capture a proximal end of an optic of the intraocular lens. The plunger may include a plunger rod, and at least a portion of the plunger rod may be angularly offset from a longitudinal axis of the plunger rod. The injector body may include an insertion depth guard disposed at a distal end of the injector body, and the insertion depth guard may include a flanged surface. A cross-sectional dimension of the insertion depth guard may be larger than a cross-sectional dimension of the nozzle. The flanged surface may be a curved surface. The plunger may include a biasing element disposed adjacent to a proximal end of the plunger. The biasing element may be deformable upon engagement with the injector body to produce a force resistive to further advancement of the plunger through the bore. The biasing element may include a channel, and wherein the body portion of the plunger may extend through the channel. A first groove may be disposed adjacent to second protrusion and adapted to receive an optic of an intraocular lens.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 2 shows a longitudinal cross-sectional view of the intraocular lens injector of FIG. 1.

FIG. 3 is a perspective view of a distal portion of an example injector body of the intraocular lens injector of FIG. 1.

FIG. 4 is a cross-sectional view of the distal portion of the injector body shown in FIG. 3.

FIG. 5 is an example cross-sectional shape of a nozzle of an intraocular lens injector.

FIG. 19 is a detail view of the distal end of the IOL injector showing a demarcation designating a pause position of an IOL being advanced through the IOL injector.

FIG. 20 is a view of a distal end 60 of an IOL injector with an IOL located therein at a pause position.

FIG. 21 is a detail view of an example IOL injector showing an opening at an interface between a compartment into which an IOL is received and an internal bore of an injector body, the detail view being transverse to a longitudinal axis of the IOL injector, and the detail view showing a flexible wall portion in contact with an injector rod.

DETAILED DESCRIPTION

Figure 1:
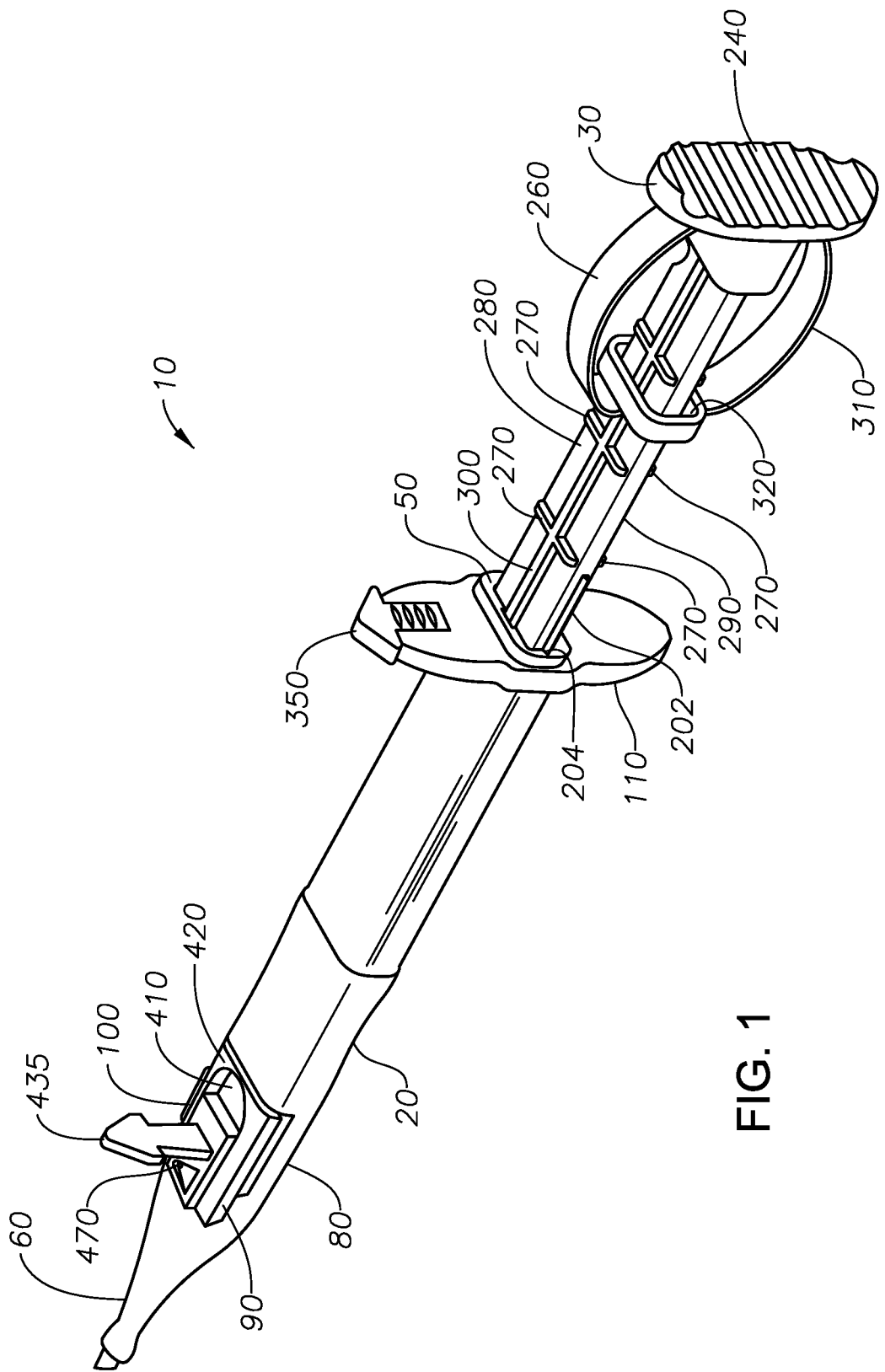
FIG. 1 is a perspective view of an example intraocular lens injector.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present disclosure relates to systems, apparatuses, and methods for delivering an IOL into an eye. FIGS. 1 and 2 show an example IOL injector 10 that includes an injector body 20 and a plunger 30. The injector body 20 defines a bore 40 extending from a proximal end 50 of the injector body 20 to a distal end 60 of the injector body 20. The plunger 30 is slideable within the bore 40. Particularly, the plunger 30 is slideable within bore 40 in order to advance an IOL, such as IOL 70, within the injector body 20. The IOL injector 10 also includes a longitudinal axis 75. The longitudinal axis 75 may extend along the plunger 30 and define a longitudinal axis of the plunger 30.

The injector body 20 includes a compartment 80 operable to house an IOL prior to insertion into an eye. In some instances, a door 90 may be included to provide access to the compartment 80. The door 90 may include a hinge 100 such that the door 90 may be pivoted about the hinge 100 to open the compartment 80. The injector body 20 may also include tabs 110 formed at the proximal end 50 of the injector body 20. The tabs 110 may be manipulated by fingers of a user, such as an ophthalmologist or other medical professional, to advance the plunger 30 through the bore 40.

FIGS. 3-5 illustrate details of the distal end 60 of the injector body 20. In some instances, the distal end 60 has a tapered exterior surface. Further, the distal end 60 includes a passage 64 that tapers towards a distal opening 125. The injector body 20 also includes a nozzle 120 at the distal end 60. The nozzle 120 is adapted for insertion into an eye so that an IOL may be implanted. An IOL is expelled from distal opening 125 formed in the nozzle 120. As shown in FIG. 5, the nozzle 120 may have an elliptical cross section. Additionally, the nozzle 120 may include a beveled tip 130. The compartment 80, passage 64, and opening 125 may define a delivery passage 127. A size of the delivery passage 127 may vary along its length. That is, in some instances, a height H1 of the passage may change along a length of the delivery passage 127. The variation in size of the delivery passage 127 may contribute to the folding of the IOL as it is advanced therealong.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the nozzle 120 is permitted to extend into an eye. In some implementations, the flanged surface 150 may have a curvature that conforms to the outer surface of an eye. For example, the flanged surface 150 may have a curvature that conforms to a scleral surface of the eye. In other instances, the flanged surface 150 may have a curvature that corresponds to a corneal surface of the eye. In still other instances, the flanged surface 150 may have a curvature, part of which corresponds to a scleral surface and another part that corresponds to a corneal surface. Thus, the flanged surface 150 may be concave. In other instances, the flanged surface 150 may be flat. In still other instances, the flanged surface 150 may be convex. Further, the flanged surface 150 may have any desired contour. For example, the flanged surface 150 may be a curved surface having radii of curvature that vary along different radial directions from a center of the flanged surface 150. In still other instances, the flanged surface 150 may define a surface that has varying curvature along different radial directions as well as curvature that varies along one or more particular radial directions.

In FIG. 3, the insertion depth guard 140 is shown as a continuous feature that forms a continuous flanged surface 150. In some implementations, the insertion depth guard 140 may be segmented into a plurality of features or protrusions forming a plurality of eye-contacting surfaces. These eye-contacting surfaces may work in concert to control the depth to which the nozzle 120 may penetrate an eye. In other implementations, the insertion depth guard 140 may be omitted.

Figure 6:
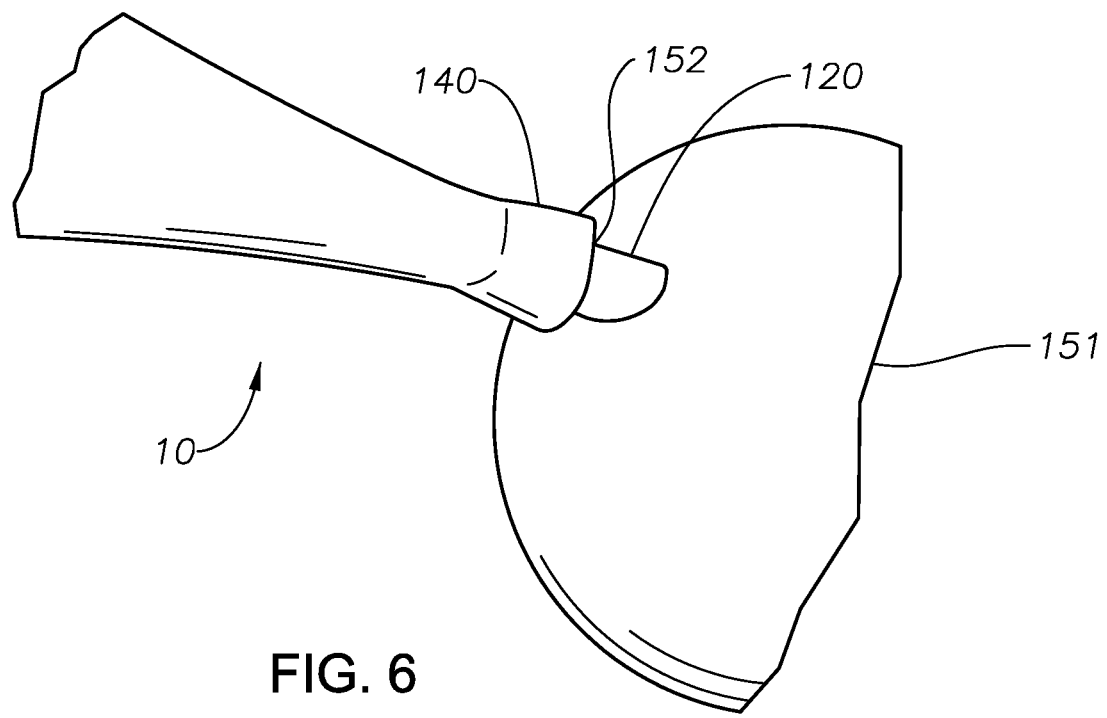
FIG. 6 shows an intraocular lens injector partially inserted into an eye.
Figure 7:
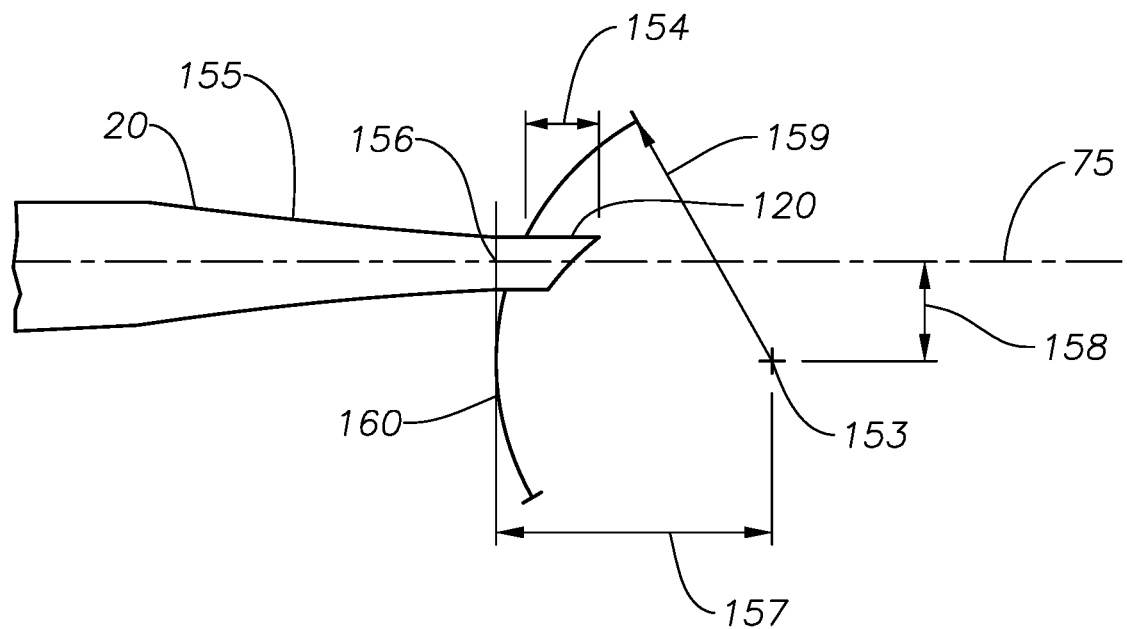
FIG. 7 shows a construction method for defining a flanged surface of an insertion depth guard of an example intraocular lens injector.

An example implementation of the insertion depth guard 140 is shown in FIGS. 6-7. In FIG. 6, the IOL injector 10 is shown with the nozzle 120 inserted into an eye 151 through a wound 152 formed in the eye. Thus, as explained above, the flanged surface 150 of the insertion depth guard 140 may be spherical in nature in order to conform to the eye 151 when the nozzle 120 is fully inserted thereinto.

FIG. 7 shows a side view of the distal portion of the IOL injector 10 showing an example layout for defining a shape of the flanged surface 150. In this illustrated example, the surface is defined to be spherical in nature. Thus, in some instances, the flanged surface may be described as a "spherical surface" which is understood to mean a surface that conforms to a sphere. A spherical surface of the flanged surface 150 may approximate the shape of an eye. However, a spherical surface is provided only as an example. Thus, the shape of the flanged surface 150 may be any desired shape.

As shown, a center 153 for use in defining a spherical surface of the flange surface 150 may be located relative to the nozzle 120 of the IOL injector 10. A center 153 of the spherical surface may be located to produce, for example, a desired length 154 of the nozzle 120 that extends beyond the flanged surface 150 and, thus, into an eye.

The injector body 20 may include a tapered portion 155. The nozzle 120 and tapered portion 155 meet at a location 156. A horizontal position of the center 153 may be made in reference to the location 156. For example, a horizontal displacement 157 of the center 153 from location 156 may be in the range of 7.6 mm to 8.0 mm. Accordingly, in some implementations, the center 153 may have a horizontal displacement of 7.6 mm, 7.7 mm, 7.8 mm, 7.9 mm, or 8.0 mm. A vertical position of the center 153 may be defined by a vertical distance 158 from the longitudinal axis 75. In some instances, the vertical displacement 158 may be 2.3 mm to 2.7 mm. Thus, in some implementations, the center 153 may have a horizontal displacement of 2.3 mm, 2.4 mm, 2.5 mm, 2.6 mm, or 2.7 mm. However, it is noted that the ranges of the horizontal displacement 157 and the vertical displacement 158 of the center 153 are provided only as examples. Thus, the values of the horizontal displacement 157 and vertical displacement 158 of the center 153 may greater or smaller than the examples provided or any value in between. Moreover, the horizontal displacement 157 and vertical displacement 158 may be any desired length.

In some implementations, a radius 159 of spherical surface 160 may be sized to correspond to a radius of an eye. In some instances, the radius 159 may be within the range of 7.5 mm to 8.1 mm. Thus, the radius may be 7.5 mm, 7.6 mm, 7.7 mm, 7.8 mm, 7.9 mm, 8.0 mm, or 8.1 mm. These values are provided only as examples. Accordingly, it is within the scope of the disclosure that the radius 159 may be greater or smaller than the values provided or any value in between. Consequently, the value of radius 159 may be any desired value.

The values of the horizontal displacement 157, vertical displacement 158, and radius 159 may be selected to produce a nozzle length 154 of any desired size. For example, in some instances, these values may be selected to produce a nozzle length 154 of between 1.0 mm and 5.0 mm. In some implementations, the length of the nozzle 120 may be 2.0 mm. In other instances, the length of the nozzle 120 may be 3.0 mm. In some instances, the nozzle 120 may be 4.0. In still other instances, the length of the nozzle 120 may be 5.0 mm. However, the scope of the disclosure is not so limited. Rather, the length of the nozzle 120 may be greater or less than the values presented or any value in between. Moreover, the length of nozzle 120 may be any desired length.

Figure 8:
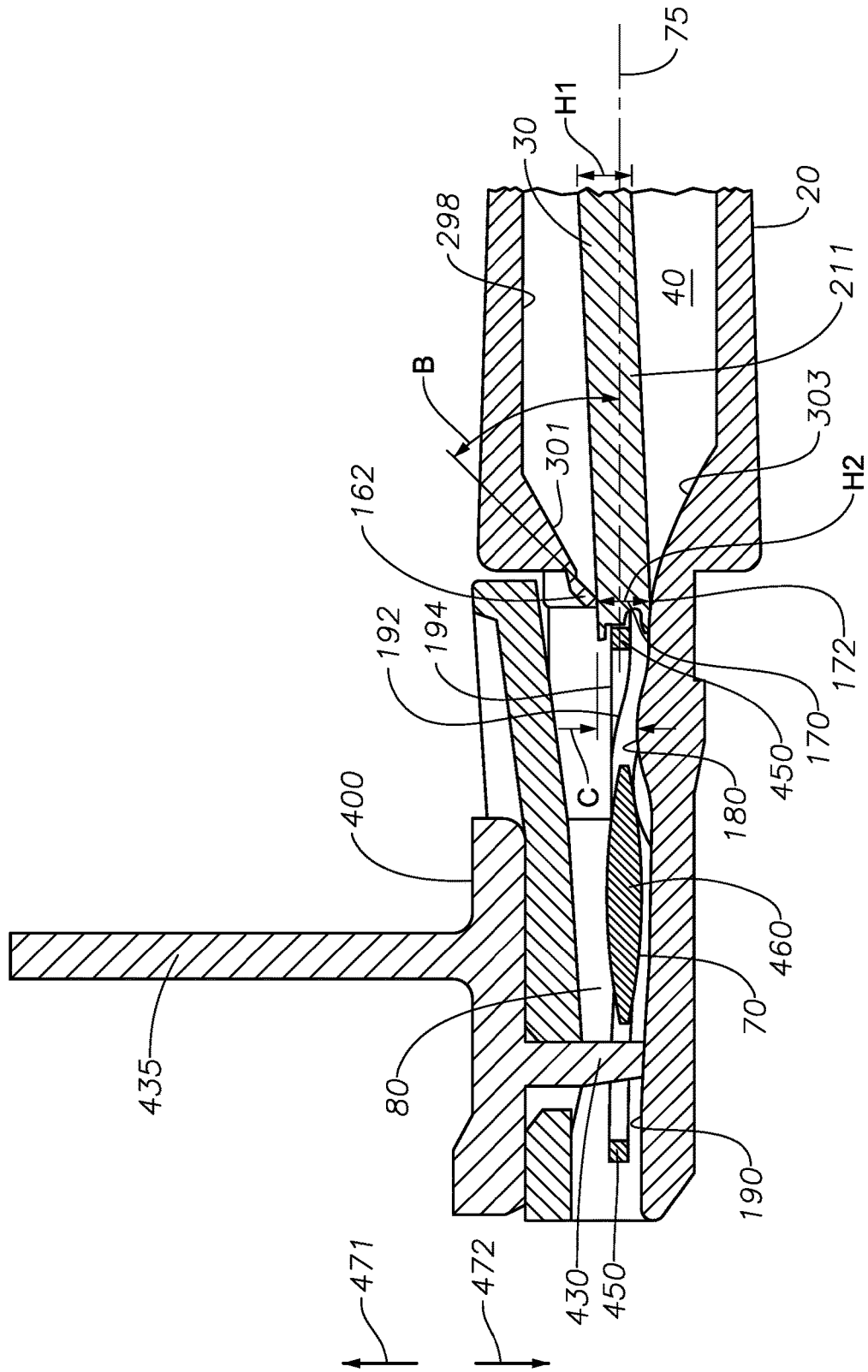
FIG. 8 shows a cross-sectional view of an intraocular lens receiving compartment formed in an injector body.
Figure 9:
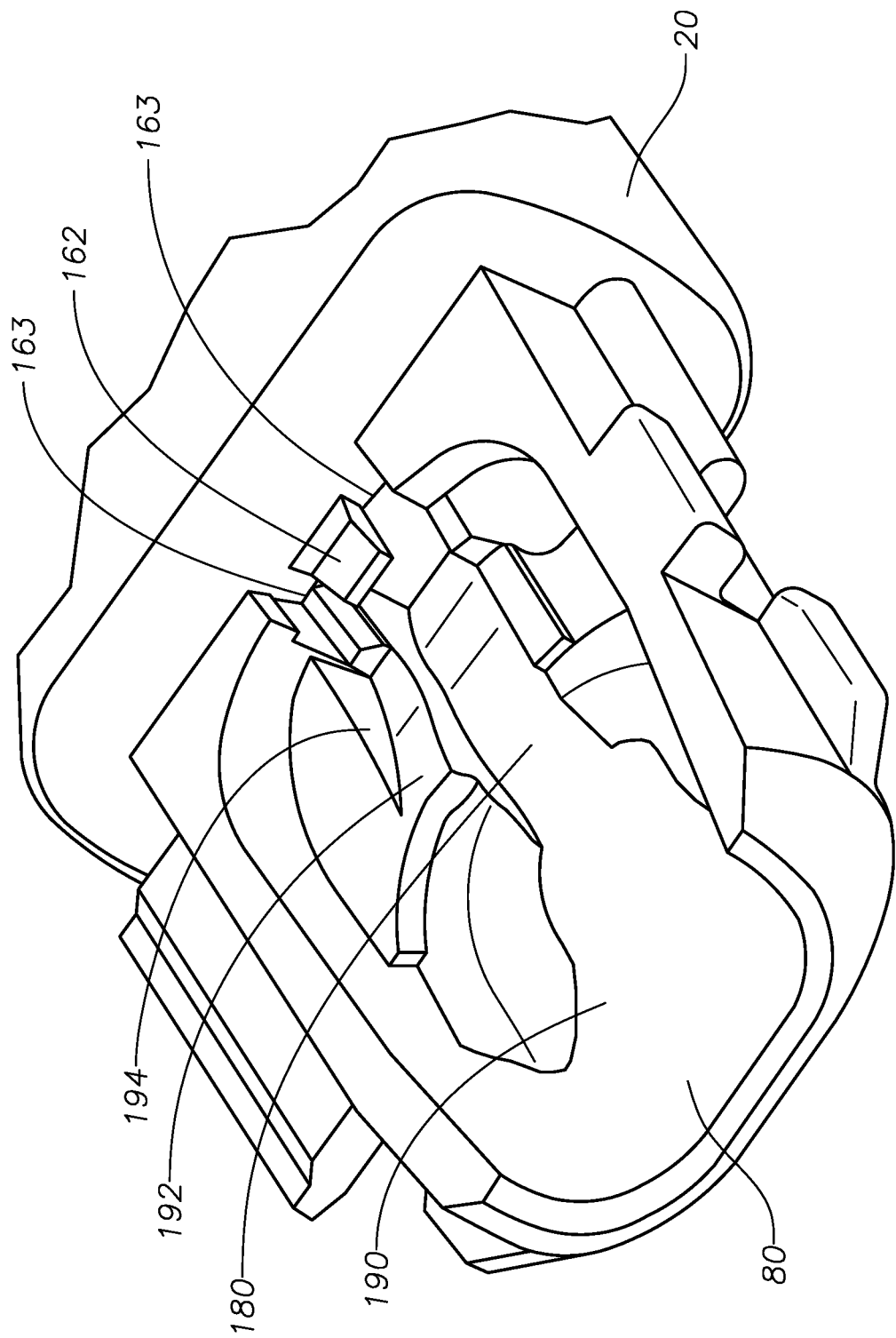
FIG. 9 shows a perspective view of an intraocular lens receiving compartment formed in an injector body.

FIG. 8 shows a cross-sectional detail view of the compartment 80 and a portion of bore 40 of the example injector body 20 shown in FIG. 2. The bore 40 is defined by an interior wall 298. The interior wall 298 includes a tapered portion that includes a first tapered wall 301 and a second tapered wall 303. The tapered portion of the interior wall 298 defines an opening 170 at an interface 172 between the bore 40 and the compartment 80. The opening 170 includes a height H1. The distal end portion 211 of the plunger rod 210 has a height of H2. In some instances, height H1 may be larger than height H2, such that, initially, there is no interference between the plunger rod 210 and the interior wall 298 at the opening 170. In other instances, height H1 may be equal to or larger than height H2, such that the plunger rod 210 and the opening 170 initially have an interference fit. In some implementations, the first tapered wall 301 includes a flexible wall portion. In the example shown, the flexible wall portion 162 is an obliquely-extending, flexible portion of the interior wall 298 and, particularly, of the first tapered wall 301. As shown in FIG. 9, in some instances, portions of the first tapered wall 301 are removed, forming voids 163 that flank the flexible wall portion 162. Thus, in some instances, the flexible wall portion 162 may extend in a cantilevered manner.

Referring again to FIG. 8, in some instances, the flexible wall portion 162 may be sloped toward the distal end 60 of the injector body 20. In some instances, an angle B defined by the flexible wall portion 162 and the longitudinal axis 75 may be in the range of 20° to 60°. For example, in some instances, the angle B may be 20°, 25°, 30°, 35°, 40°, 45°, 50°, 55°, or 60°. Further, the angle B may be greater or smaller than the defined range or anywhere within the recited range. Moreover, the scope of the disclosure is not so limited. Thus, the angle B may be any desired angle.

The injector body 20 may also include a contoured ramp 180 formed along an interior receiving surface 190 of the compartment 80. Generally, the interior receiving surface 190 is the surface on which an IOL, such as IOL 70, is placed when loaded into the IOL injector 10. FIG. 9 is a perspective view of a portion of the example injector body 20 shown in FIG. 2. The door 90 is not shown. In some instances, a vertical distance C between a tip of the flexible wall portion 162 and the top of the contoured ramp 180 may correspond with a height H2 of a distal end portion 211 of the plunger rod 210. In other instances, the distance C may be greater or less than the height H2 of the distal end portion 211 of the plunger rod 210. The flexible wall portion 162 and contoured ramp 180 are discussed in more detail below.

As also shown in FIG. 9, the injector body 20 may include a contoured surface 192 that is offset from the receiving surface 190. A wall 194 is formed adjacent to the contoured surface 192. A freely extending end 452 of a haptic 450 contacts the contoured surface 192 when IOL 70 is received into the compartment 80.

Figure 10:
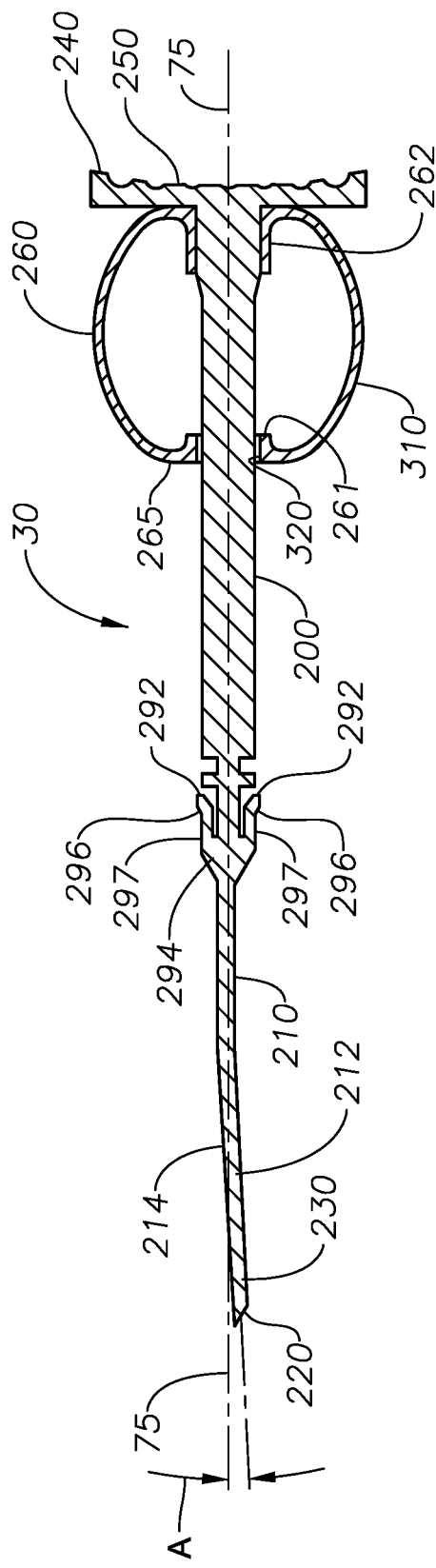
FIG. 10 is a cross-sectional view of a plunger.
Figure 11:
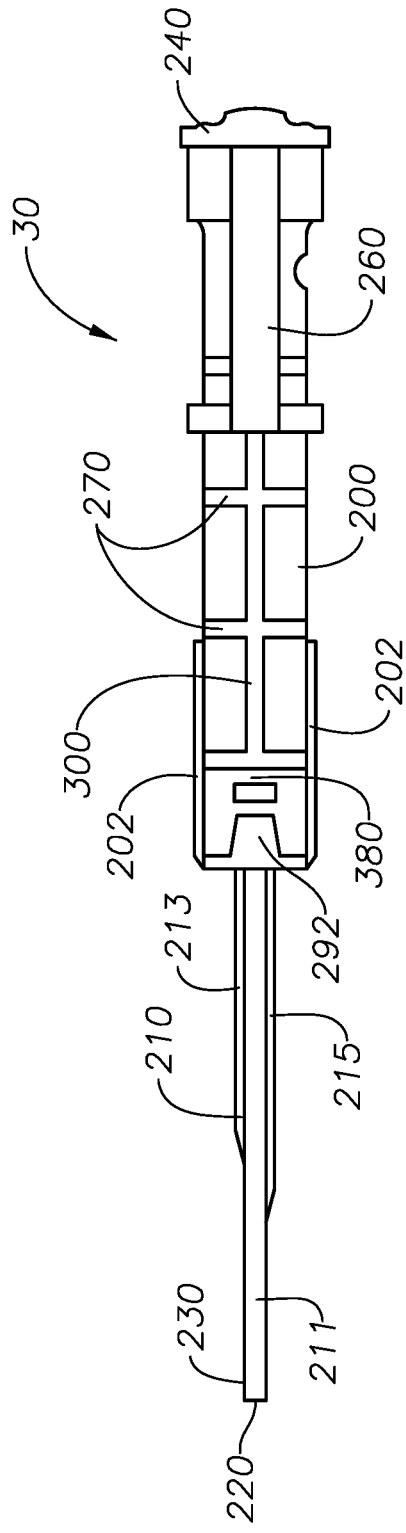
FIG. 11 is a bottom view of a plunger.

Referring to FIGS. 1 and 10-11, the plunger 30 may include a body portion 200, a plunger rod 210 extending distally from the body portion 200, and a plunger tip 220 formed at a distal end 230 of the plunger rod 210. The plunger 30 may also include a flange 240 formed at a proximal end 250 of the body portion 200. A biasing element 260 may be disposed on the plunger 30. In some instances, the biasing element 260 may be a spring. In some implementations, the biasing element 260 may be disposed adjacent to the flange 240. A proximal end 262 may be fixedly attached at the body portion adjacent to the flange 240. In other instances, the biasing element 260 may be disposed at another location along the body portion 200. In still other implementations, the biasing element 260 may be formed or otherwise disposed on the injector body 20 and adapted to engage the plunger 30 at a selected location during advancement of the plunger 30 through bore 40.

The flange 240 may be used in concert with the tabs 110 to advance the plunger 30 through the injector housing 20. For example, a user may apply pressure to tabs 110 with two fingers while applying opposing pressure to the flange 240 with the user's thumb. A surface of the flange 240 may be textured in order to provide positive gripping by a user. In some instances, the texture may be in the form of a plurality of grooves. However, any desired texture may be utilized.

The body portion 200 may include a plurality of transversely arranged ribs 270. In some instances, the ribs 270 may be formed on both a first surface 280 and a second surface 290 of the body portion 200. In other instances, the ribs 270 may be formed on only one of the first surface 280 and second surface 290. A longitudinally extending rib 300 may also be formed on one or both of the first and second surfaces 280, 290.

In some instances, the body portion 200 may also include one or more protrusions 202, as shown in FIG. 11. The protrusions 202 may extend longitudinally along a length of the body portion 200. The protrusions 202 may be received grooves 204 formed in the injector body 20, as shown in FIG. 1. The protrusions 202 and grooves 204 interact to align the plunger 30 within the bore 40 of the injector body 20.

The body portion 220 may also include cantilevered members 292. The cantilevered members 292 may extend from a proximal end 294 of the body portion 200 towards the distal end 250. The cantilevered members 292 may include flared portions 296. The cantilevered members 292 may also include substantially horizontal portions 297. The flared portions 296 are configured to engage the interior wall 298 of the injector body 20 that defines the bore 40, as shown in FIG. 2. Engagement between the cantilevered members 292 and the interior wall 298 generates a force resistive to advancement of the plunger 30 and provides a tactile feedback to the user during advancement of the plunger 30. For example, in some implementations, the resistive force generated by contact between the cantilevered members 292 and the interior wall 298 may provide a baseline resistance that resists advancement of the plunger 30.

In some instances, the plunger rod 210 may include an angled portion 212. The distal end portion 211 may form part of the angled portion 212. The angled portion 212 may define an angle, A, within the range of 1° to 5° with the longitudinal axis 75. In some instances, the angle A maybe 2°. In some instances, the angle A may be 2.5°. In still other instances, the angle A may be 3°, 3.5°, 4°, 4.5°, or 5°. Further, while the above values of A are provided as examples, the angle A may be greater or less than the indicated range or any value in between. Thus, the angle A may be any desired angle.

The angled portion 212 ensures that the plunger tip 220 contacts and follows the receiving surface 190 as the plunger 30 is advanced through the bore 40. Particularly, the angle A defined by the angled portion 212 exceeds what is needed to cause the plunger tip 220 to contact the interior wall 298 of the bore 40. That is, when the plunger 30 is disposed within the bore 40, engagement between the plunger tip 220 and the interior wall 298 causes the angled portion 212 to bend inwardly due to the angle A. Consequently, the angled portion 212 ensures that the plunger tip 220 properly engages the haptics and optic of an IOL being inserted from the IOL injector 10. This is described in greater detail below. Although the angled portion 212 is shown as being a substantially straight portion bent at an angle relative to the remainder of the plunger rod 210, the scope is not so limited. In some instances, a portion of plunger rod 210 may have a continuous curvature. In other instances, an entire length of the plunger rod 210 may be bent or have a curvature. Further, the amount of angular offset from the longitudinal axis 75 or amount of curvature may be selected in order to provide a desired amount of engagement between the plunger tip 220 and the interior surfaces of the injector body 20.

The biasing element 260 may be affixed to the body portion 200 adjacent to the flange 240. In some instances, the biasing element 260 may form a hoop 310 extending distally along the body portion 200 that functions as a spring to resist advancement of the plunger 30 when the hoop 310 engages the injector body 20. The biasing element 260 may also include a collar 261 channel 320 through which the body portion 200 extends. Thus, in operation, as the plunger 30 is advanced through the bore 40 of the injector body 20 (i.e., in the direction of arrow 330), a distal end 265 of the biasing element 260 contacts the proximal end 50 of the injector body 20 at a selected location along the stroke of the plunger 30. As the injector 30 is further advanced, the biasing element 260 is compressed and the channel 320 permits the distal end 265 of the biasing element 260 to move relative to the body portion 200. Similarly, the channel 320 permits relative movement between the body portion 200 and the distal end 265 of the biasing element 260 during proximal movement of the plunger 30 (i.e., in the direction of arrow 340).

Figure 16:
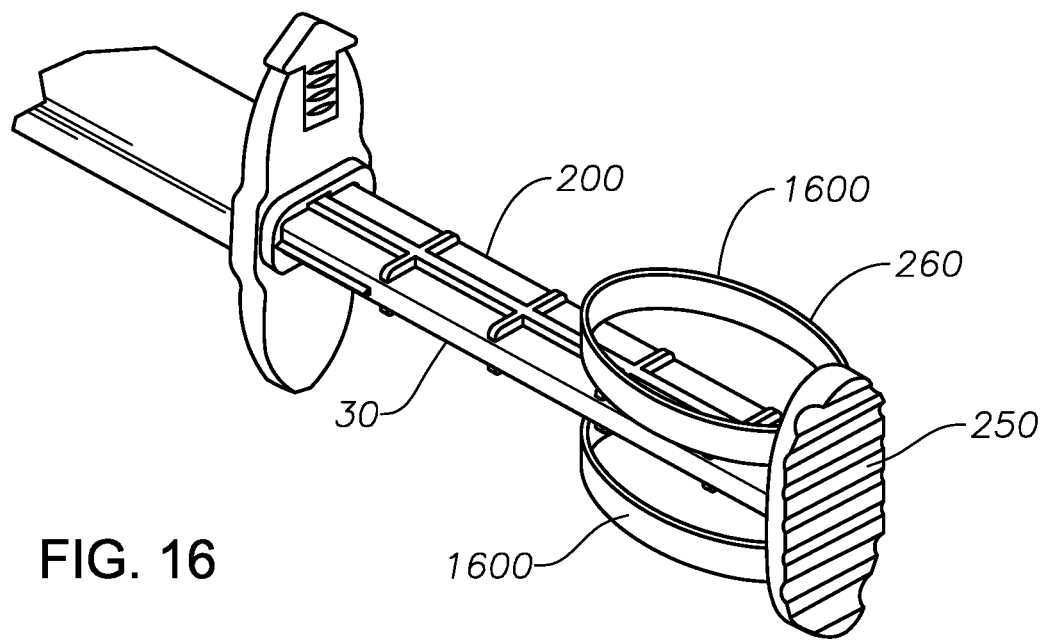
FIG. 16 is a detail view of a plunger with another example biasing element design.
Figure 17:
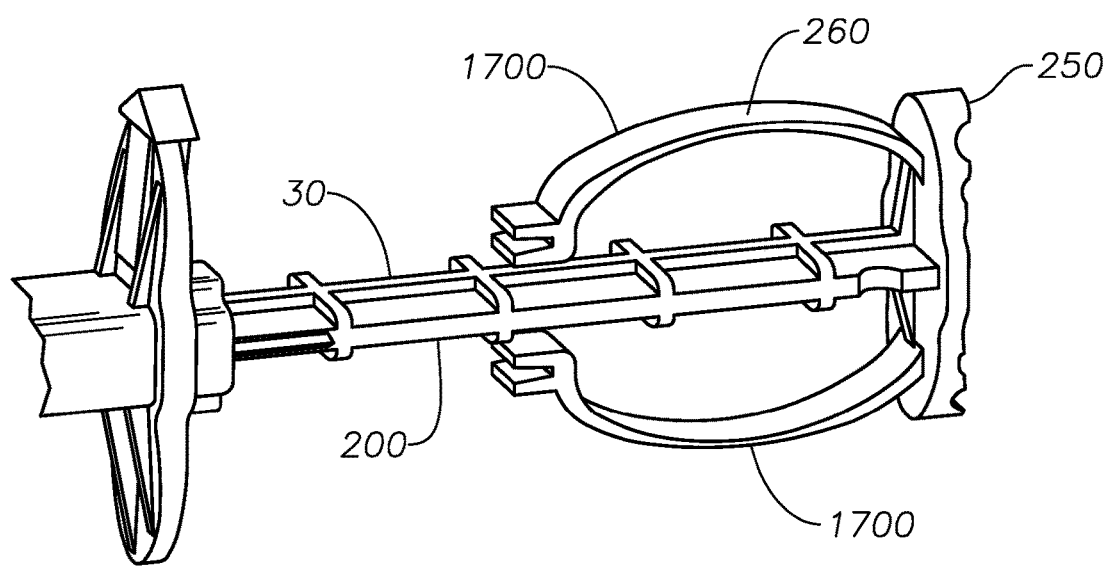
FIG. 17 illustrates a plunger having yet another example biasing element design.
Figure 18:
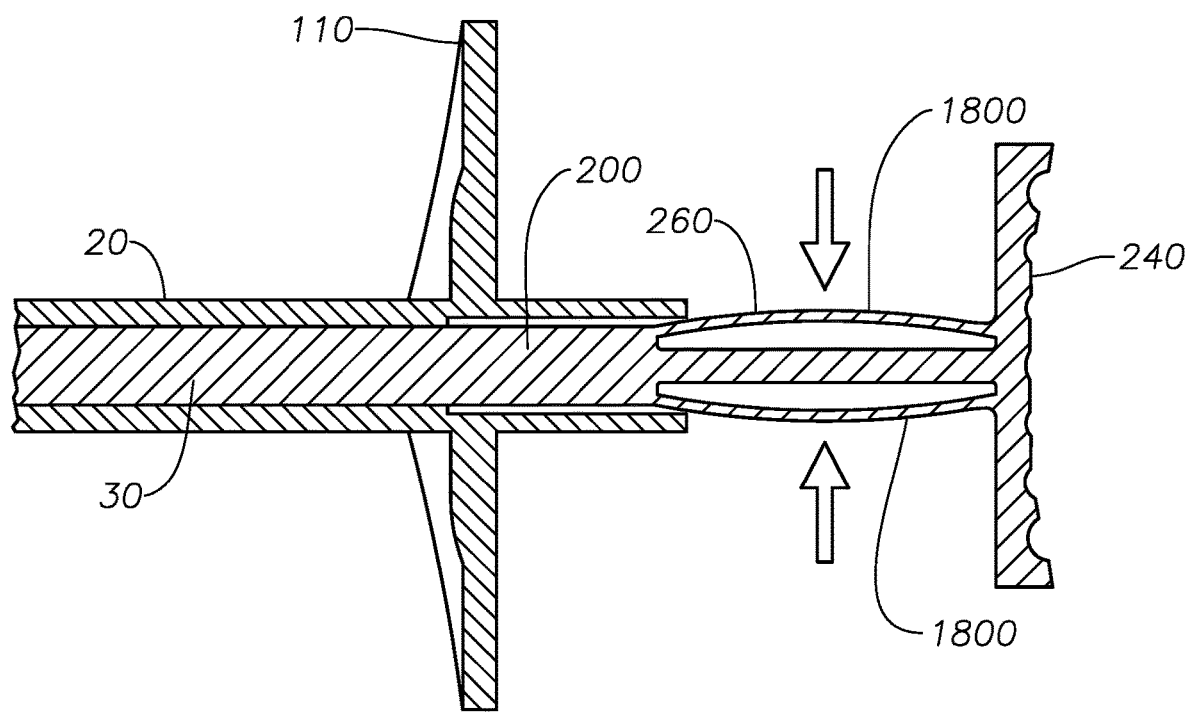
FIG. 18 shows another plunger with a further example biasing element design.

The biasing element 260 in the form of hoop 310, shown, for example, in FIG. 2, is provided merely as an example. The biasing element 260 may have other configurations. For example, FIG. 16 illustrates a biasing element having elongated elliptical or oval members 1600 disposed on opposite sides of the body portion 200 of the plunger 30 and attached to the flange 240. FIG. 17 shows another example configuration of the biasing element 260. In FIG. 17, the biasing element 260 is in the form of curved, cantilevered members 1700 provided on opposing sides of the body portion 200 of the plunger 30. The cantilevered members 1700 are attached to the flange 240. FIG. 18 shows an example in which the biasing element 260 is integrated into the body portion 200 of the plunger 30. The biasing element 260 includes arcuate members 1800 that engage an interior wall that defines the bore 40 of the injector body 20. While some examples are provided, the scope of the disclosure is not so limited. Rather, biasing elements having other forms and configurations are included within the scope of the disclosure.

Figure 12:
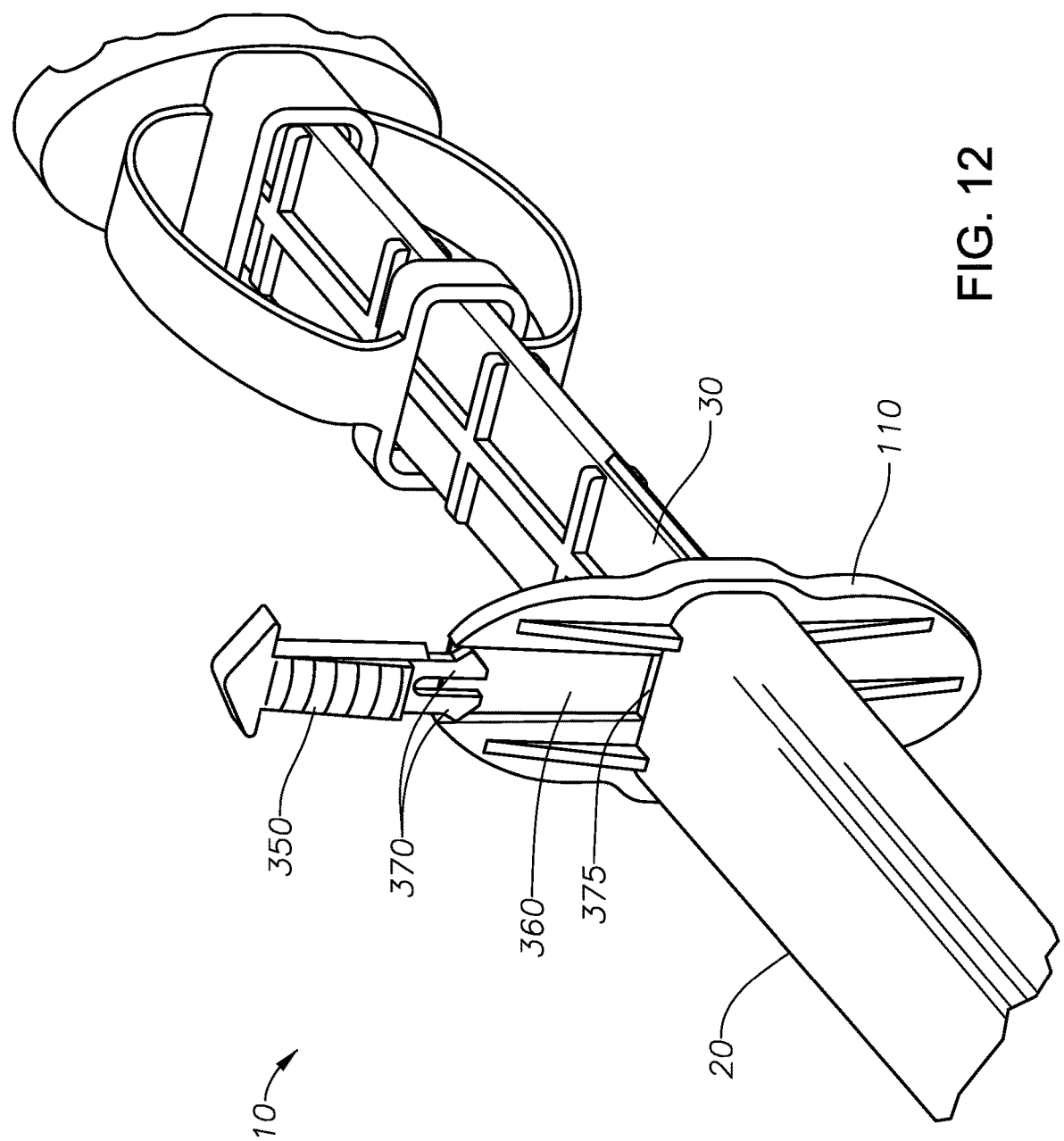
FIG. 12 is a partial perspective view showing tabs and a plunger lock of an example intraocular lens injector.

Referring to FIGS. 2, 11, and 12, the IOL injector 10 may also include a plunger lock 350. The plunger lock 350 is removably disposed in a groove 360 formed in one of the tabs 110. The plunger lock 350 includes a protrusion 370 formed at one end thereof. The plunger lock 350 may include a single protrusion 370, as shown in FIG. 2. In other instances, the plunger lock 350 may include a plurality of protrusions 370. For example, FIG. 12 illustrates an example plunger lock 350 having two protrusions 370. In other instances, the plunger lock 350 may include additional protrusions 370.

When installed, the protrusion 370 extends through an aperture 375 formed in the injector body 20 and is received into a slot 380 formed in the plunger 30. When the plunger lock 350 is installed, the protrusion 370 and slot 380 interlock to prevent the plunger 30 from moving within the bore 40. That is, the installed plunger lock 350 prevents the plunger 30 from being advanced through or removed from the bore 40. Upon removal of the plunger lock 350, the plunger 30 may be freely advanced through the bore 40. In some instances, the plunger lock 350 may include a plurality of raised ribs 390. The ribs 390 provide a tactile resistance to aid in removal from and insertion into groove 360.

The plunger lock 350 may be U-shaped and define a channel 382. The channel 382 receives a portion of the tab 110. Further, when fitted onto the tab 110, a proximal portion 384 of the plunger lock 350 may be outwardly flexed. Consequently, the plunger lock 350 may be frictionally retained on the tab 110.

Referring to FIGS. 2 and 10, in some implementations, the body portion 20 may include shoulders 392 formed in bore 40. The shoulders 392 may be formed at a location in the bore 40 where the bore 40 narrows from an enlarged proximal portion 394 and a narrower distal portion 396. In some instances, the shoulder 392 may be a curved surface. In other instances, the shoulder 392 may be defined a stepped change in the size of bore 40.

The cantilevered members 292 may engage the shoulder 392. In some implementations, the flared portion 296 of the cantilevered members 292 may engage the shoulder 392. In some instances, a location at which the cantilevered members 292 engage the shoulder 392 may be one in which the slot 380 aligns with the aperture 375. Thus, in some implementations, engagement between the cantilevered members 292 and shoulder 392 may provide a convenient arrangement for insertion of the plunger lock 350 to lock the plunger 30 in place relative to the injector body 20. In other implementations, the slot 380 and the aperture 375 may not align when the cantilevered members 292 engage the shoulder 392.

As the plunger 30 is advanced through the bore 40, the flared portion 296 of the cantilevered members 292 may be inwardly displaced to comply with the narrowed distal portion 396 of the bore 40. As a result of this deflection of the flared portion 296, the cantilevered members 292 apply an increased normal force to the interior wall 298 of the bore 40. This increased normal force generates a frictional force that resists advancement of the plunger 30 through bore 40, thereby providing tactile feedback to the user.

Figure 27:
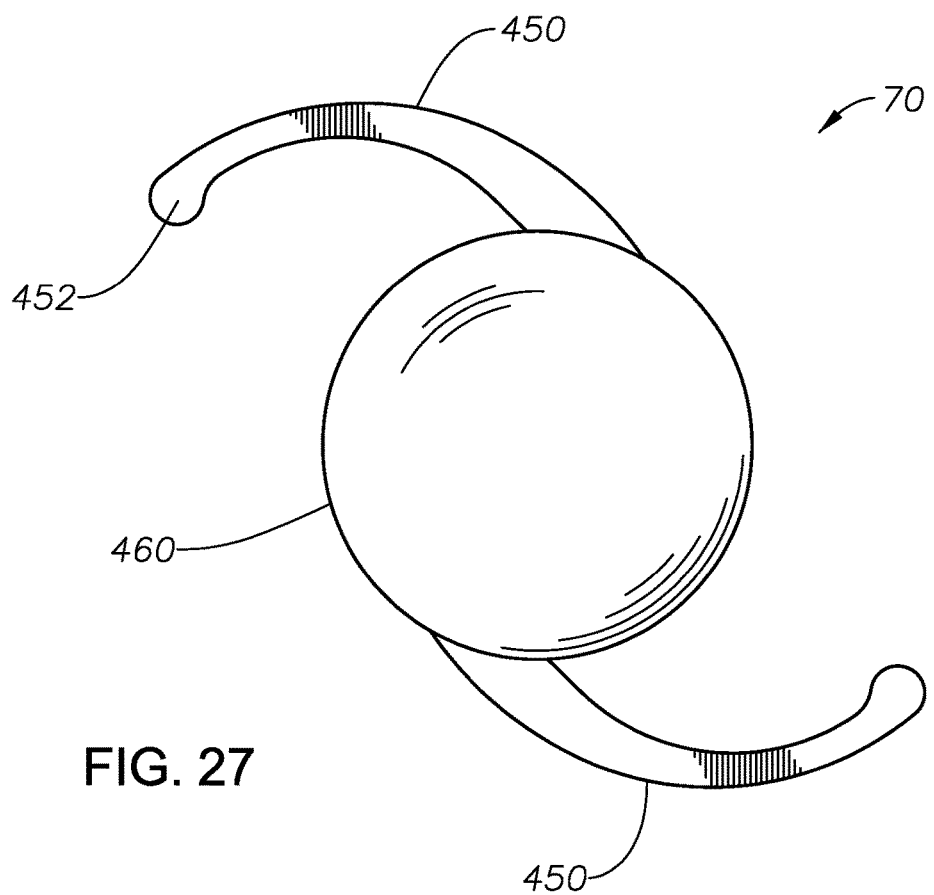
FIG. 27 shows an example IOL.

Referring to FIGS. 1 and 2, the IOL injector may also include an IOL stop 400. The IOL stop 400 is received into a recess 410 formed in an outer surface 420 the door 90. The IOL stop 400 may include a protrusion 430 that extends through an opening 440 formed in the door. The protrusion 430 extends between a haptic and optic of an IOL loaded into the compartment 80. As shown in FIGS. 1 and 27, the IOL 70 includes haptics 450 and an optic 460. The protrusion 430 is disposed between one of the haptics 450 and the optic 460. The IOL stop 430 may also include a tab 435. The tab 435 may be gripped by a user for removal of the IOL stop 430 from the injector body 20.

The IOL stop 400 may also include an aperture 470. The aperture 470 aligns with another opening formed in the door 90, for example opening 472 shown in FIG. 19. The aperture 470 and second opening 472 in the door 90 form a passageway through which a material, such as a viscoelastic material, may be introduced into the compartment 80.

The IOL stop 400 is removable from the door 90. When installed, the IOL stop 400 prevents advancement of the IOL, such as IOL 70. Particularly, if advancement of the IOL 70 is attempted, the optic 460 contacts the protrusion 430, thereby preventing advancement of the IOL 70.

Figure 13:
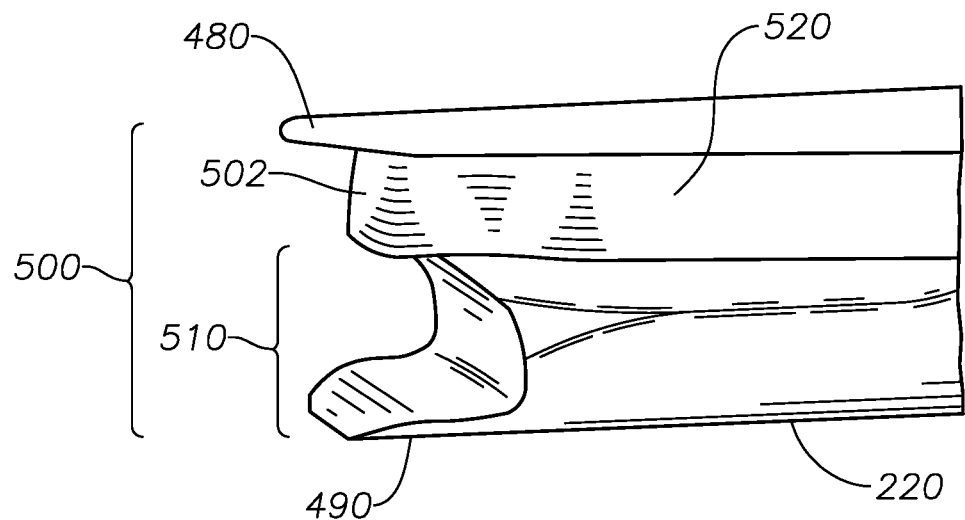
FIG. 13 is a detail view of an example plunger tip of plunger.

FIG. 13 shows an example plunger tip 220. The plunger tip 220 may include a first protrusion 480 and a second protrusion 490 extending from opposing sides. The first and second protrusions 480, 490 define a first groove 500. The first groove 500 defines a surface 502. A second groove 510 is formed within the first groove 500. The first groove 500, particularly in combination with the first protrusion 480, serves to capture and fold a trailing haptic of an IOL. The second groove 510 functions to capture and fold an optic of an IOL.

A side wall 520 of the plunger tip 220 may be tapered. The tapered side wall 520 may provide a nesting space for a gusseted portion of the trailing haptic of an IOL. The gusseted portion of the haptic tends to remain proximal to the IOL optic. Thus, the tapered side wall 520 may provide a nesting space that promotes proper folding of the IOL during delivery into an eye.

Figure 28:
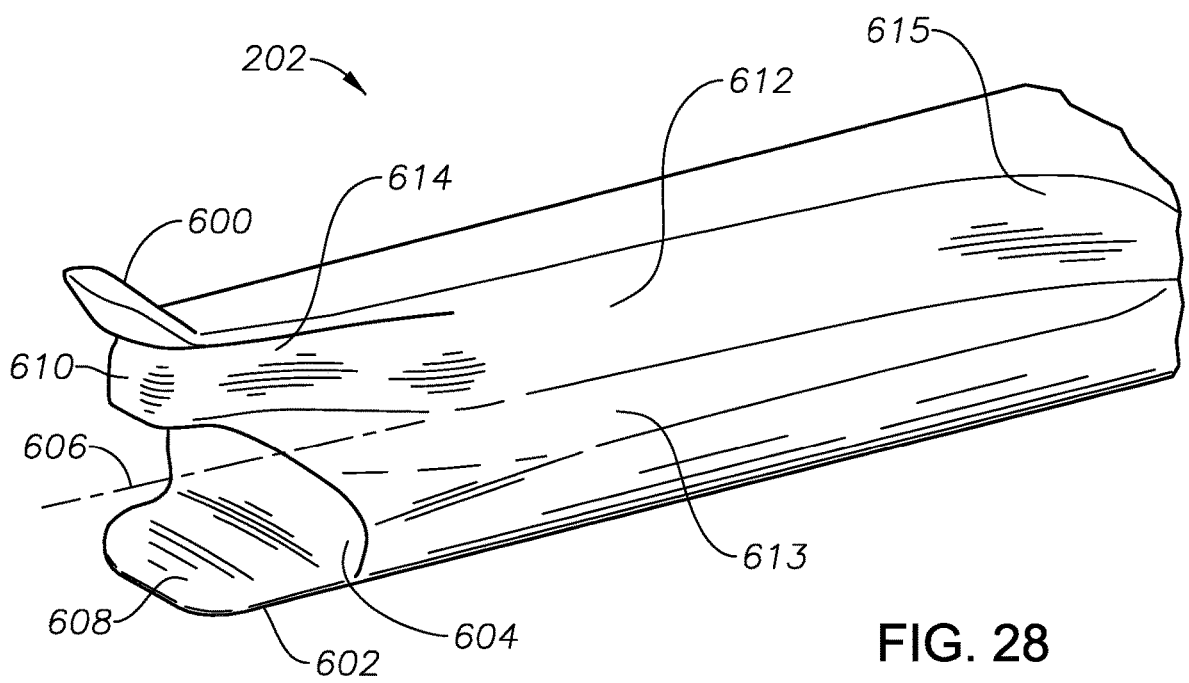
FIG. 28 is a perspective view of an example plunger tip.
Figure 29:
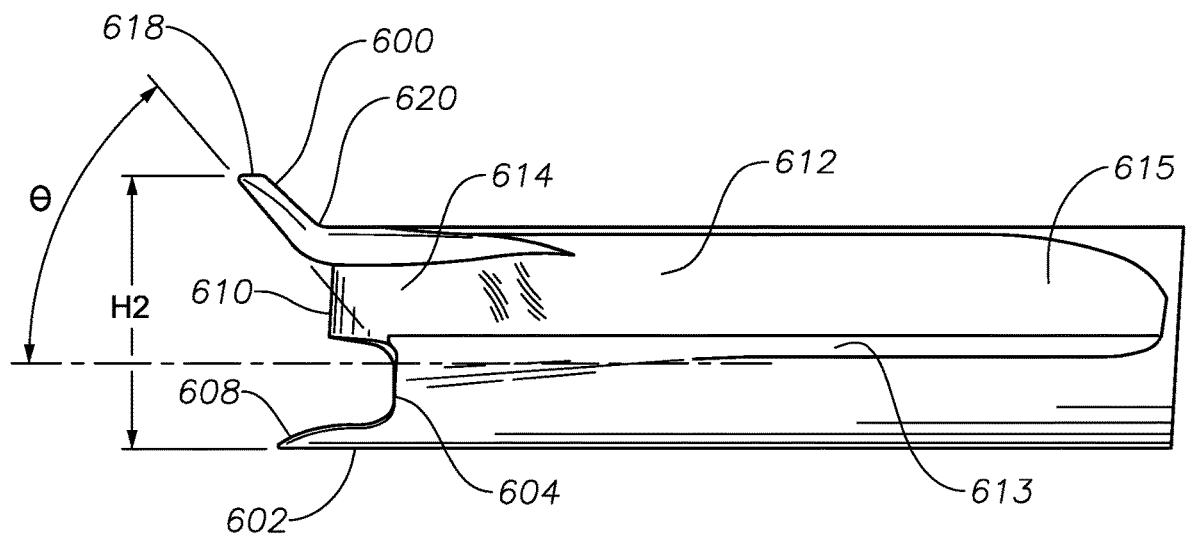
FIG. 29 is a side view of the example plunger tip of FIG. 28.
Figure 30:
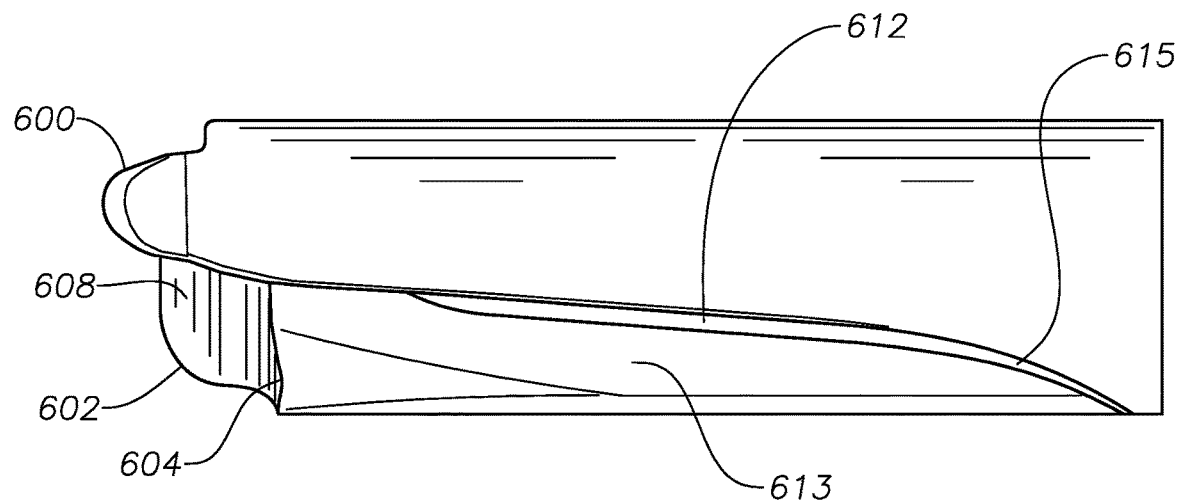
FIG. 30 is a top view of the example plunger tip of FIG. 28.

FIGS. 28-30 show another example plunger tip 220. This plunger tip 220 includes a first protrusion 600, a second protrusion 602, and a groove 604. The first protrusion extends at an oblique angle $\theta$ from longitudinal axis 606. In some instances, the angle $\theta$ may be between 25° to 60°. In other instances, the angle $\theta$ may be lower than 25° or larger than 60°. In other instances, the angle $\theta$ may be between 0° to 60°. In still other implementations, the angle $\theta$ may be between 0° and 70°; 0° and 80°; or 0° and 90°. Generally, the angle $\theta$ may be selected to be any desired angle. For example, the angle $\theta$ may selected based on one or more of the following: (1) a size, such as a height, of passage 64 formed within the nozzle 60; (2) the height of the compartment 80; (3) how the height of the passage 64 and/or compartment varies along their respective lengths; and (3)

the thickness of the plunger tip 220. The second protrusion 602 may include a tapered portion 608. The tapered portion 608 is operable to engage an optic of an IOL, such as optic 460 shown in FIG. 27. The optic may slide along the tapered surface so that the optic may be moved into the groove 604. As a result, the second protrusion 602 is positioned adjacent to a surface of the optic.

The example plunger tip 220 shown in FIGS. 28-30 also include a surface 610 that may be similar to the surface 502. The surface 610 is adapted to contact and displace a trailing or proximally extending haptic, such as haptic 450 shown in FIG. 27, so that the haptic folds. In some instance, the surface 610 may be a flat surface. In other instances, the surface 610 may be a curved or otherwise contoured surface. The example plunger tip 220 may also include a side wall 612 and support surface 613. Similar to the side wall 520, the side wall 612 may be tapered, as shown in FIG. 30. In some instances, the side wall 612 may include a first curved portion 614. The first curved portion 614 may receive a bent portion of the trailing haptic that remains proximal to the optic during folding. The trailing haptic is supported by support surface 613 during the folding process. The side wall 612 may also include a second curved surface 615.

The obliquely-extending first protrusion 600 effectively increases a height H2, as compared to the plunger tip 220 shown in FIG. 13, for example. This increased height H2 improves the ability of the plunger tip 220 to capture the trailing haptic during advancement of the plunger 30. In operation, as the plunger 30 is advanced distally, the distal end 618 engages an interior wall of the delivery passage 127 due to changes in the height H1 of the delivery passage 127. As the height H1 decreases, the first protrusion 600 pivots about hinge 620, effectively reducing the total height H2 of the plunger tip 220. As the first protrusion 600 pivots about hinge 620 and rotated in a direction towards the second protrusion 602, the first protrusion 600 captures the trailing haptic between the optic of the IOL and the first protrusion 600. Therefore, with the first protrusion 600 pivotable about the hinge 620, the size of the plunger tip 220 is able to adapt and conform to the changing height H1 of the delivery passage 127 as the IOL is advanced distally and folded.

Figure 14:
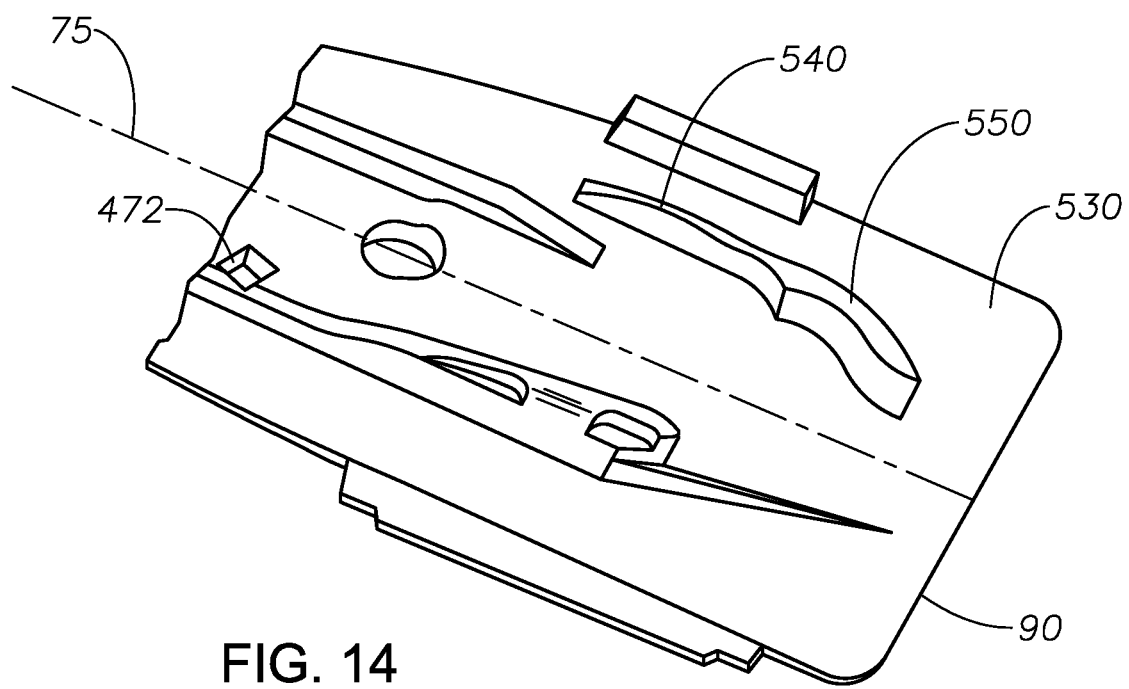
FIG. 14 shows an example interior surface of a door enclosing a lens-receiving compartment of an intraocular lens injector.

FIG. 14 shows an interior surface 530 of door 90. The surface 510 may include a ridge 530. The ridge 530 may include a curved portion 540. In the example illustrated, the curved portion 540 extends proximally and inwardly towards the longitudinal axis 75. The curved portion 540 is configured to overlay a portion of a trailing haptic of an IOL, which promotes proper folding of the IOL when the plunger 30 is advanced through the injector body 20.

In operation, the plunger lock 350 may be inserted into the groove 360 to lock the plunger 30 in position relative to the injector body 20. An IOL, such as IOL 70, may be loaded into the compartment 80. For example, the door 90 may be opened by a user and a desired IOL inserted into the compartment 80. The door 90 may be closed upon insertion of the IOL into the compartment 80. In some instances, an IOL may be preloaded during manufacturing.

The IOL stop 400 may be inserted into the recess 410 formed in the door 90. Viscoelastic material may be introduced into the compartment 80 via the aligned aperture 470 and corresponding opening formed in the door 90. The viscoelastic material functions as a lubricant to promote advancement and folding of the IOL during advancement and delivery of the IOL into an eye. In some instances, the viscoelastic material may be introduced into the compartment 80 at the time of manufacturing.

Figure 15:
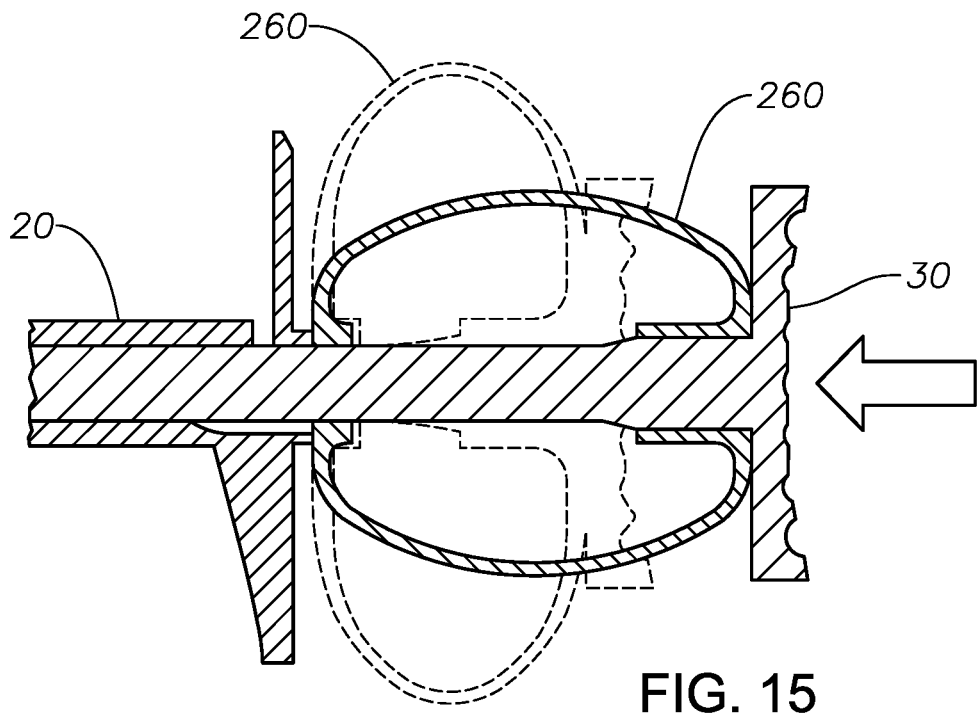
FIG. 15 shows deformation experienced by an example spring during advancement of a plunger of an intraocular lens injector.

The IOL stop 400 may be removed from the recess 410 formed in the door 90, and the plunger lock 350 may be removed from the groove 360. The plunger 30 may be advance through the bore 40. Sliding engagement between the cantilevered members 292 and the interior wall 298 of the injector body 20 generates a resistive force that resists advancement of plunger 30. In some instances, the plunger 30 may be advanced through the bore 40 until the plunger tip 220 extends into the compartment 80. For example, the plunger 30 may be advanced until the plunger tip 220 is adjacent to or in contact with the IOL. In other instances, the plunger 30 may be advanced through the bore 40 such that the IOL is partially or fully folded. Further, the plunger 30 may advance the IOL to a position within the nozzle just short of being ejected from the distal opening 125. For example, in some instances, advancement of the plunger 30, prior to insertion of the nozzle 120 into a wound formed in the eye, may be stopped at the point where the distal end 265 of the biasing element 260 contacts the proximal end 50 of the injector body 20, as shown in FIG. 15.

Advancement of the plunger 30 through the injector body 20 is discussed below with reference to FIGS. 1, 8, and 13. In some instances, dimensional tolerances between the plunger 30 and the injector body 20 may permit relative movement between the plunger 30 and the injector body 20 such that the distal end portion 211 is able to move within bore 40 in the direction of arrows 471, 472 (referred to hereinafter as "tolerance movement"). In instances, particularly those in which the plunger 30 includes angled portion 212, the plunger tip 220 normally remains in contact with the interior wall 298 even if the plunger 30 experiences tolerance movement as the plunger 30 advances through bore 40. Thus, in some instances, notwithstanding any tolerance movement, the plunger tip 220 remains in contact with the interior wall 298. Accordingly, the second tapered wall 303 directed and centers the plunger tip 220 into the opening 170.

If the plunger 30 experiences tolerance movement such that the plunger tip 220 no longer contacts the interior wall 298 of the bore 40, the first tapered wall 301, which includes the flexible wall portion 162, directs and centers the plunger tip 220 into the opening 170 formed at the interface 172, resulting in contact between the plunger tip 220 and the second tapered wall 303. When the plunger 30 becomes fully engaged with the injector body 20, the tolerance movement is substantially reduced or eliminated, ensuring that the plunger tip 220 remains engaged with the second tapered wall 303 and contoured ramp 180. In some instances, full engagement between the plunger 30 and the injector body 20 occurs when the cantilevered members 292 are fully engaged with the interior wall 298 of the bore 40. Consequently, in instances where tolerance movement may exist, upon full engagement between the plunger 30 and the injector body 20, the flexible wall portion 162 no longer influences the position of the plunger 30. In any case, once the plunger tip 220 advances through opening 170, the flexible wall portion 162 no longer affects the directional path of plunger 30 nor any part thereof.

As the plunger tip 220 is advanced through the compartment 80 in sliding contact with the receiving surface 190, the first groove 500 of the plunger tip 220 is positioned to engage the trailing haptic of IOL, such as trailing haptic 450 of IOL 70, as shown in FIG. 8. As the plunger tip 220 is further advanced, the plunger tip 220 encounters the contoured ramp 180 and is forced vertically towards the door 90. This vertical displacement of the plunger tip 220, while remaining in contact with the receiving surface 190, both folds the trailing haptic up over the optic of the IOL as well as align the second groove 510 of the plunger tip 220 with a trailing edge of the haptic. Particularly, the surface 502 of the plunger tip 220 contacts and displaces the haptic 450 as the plunger tip 220 is passed along the contoured surface 180, thereby folding the trailing haptic 450. As the trailing haptic 450 folds, the contoured surface 192 and wall 194 work in concert to both locate the freely extending end 452 of the trailing haptic 450 above and over the optic 460. The profile of the contoured surface 192 operates to lift the trailing haptic 450 as the plunger tip 220 is displaced towards the distal end 60 of the injector body 20. The wall 194 constrains lateral movement of the freely extending end 452 of the trailing haptic 450, which cause the haptic to move distally relative to the optic 460. Consequently, the trailing haptic 450 is both raised above and folded over the optic 460 as the plunger tip 220 contacts the trailing haptic 450 and follows along the contoured ramp 180. As the plunger tip 220 is further advanced, the second groove 510 accepts the trailing edge of the optic 460, and the plunger tip 220 is displaced vertically away from the door 90 due to a combination of influences from both the decreasing slope of the contoured ramp 180 and the angled portion 212 of the plunger rod 210. Movement of the plunger tip 220 in the manner described provides for improved engagement and folding of the IOL 70.

FIG. 19 is a detail view of a portion of the distal end 60 of the injector body 20. The distal end 60 includes a tapered portion 62 and the insertion depth guard 140. The distal end 265 of the biasing element 260 may engage the proximal end 50 of the injector body 20 to define a pause location of the folded or partially folded IOL. The nozzle 120 may include a demarcation 1900 that provides a visual indication of the pause position. For example, in the example shown in FIG. 19, the demarcation 1900 is a narrow ridge or line that encircles all or a portion of the distal end 60. In some instances, the demarcation 1900 may be disposed between the tapered portion 62 and the insertion depth guard 140. At least a portion of the injector body 20 may be formed form a transparent or semi-transparent material that permits a user to see an IOL within the injector body 20. Particularly, the distal end 60 of the injector body 20 may be formed from a transparent material to permit observation of the IOL as it is moved therethrough by the plunger 30.

FIG. 20 shows a view of the distal end 60 of the IOL injector 10 with IOL 70 located therein at a pause position. As shown in FIG. 20, the pause position of the IOL may be defined as a location where the distal edge 462 of optic 460 of the IOL 70 substantially aligns with the demarcation 1900. A haptic 450 or a portion thereof may extend beyond the demarcation 1900. Again, the pause position may also correspond to the initial engagement of the distal end 265 of the biasing element 260 with the proximal end 50 of the injector body 20. Therefore, the pause location may be jointly indicated by positioning of the IOL, or part thereof, relative to the demarcation 1900 and the initial contact between the distal end 265 of the biasing element 260.

In other instances, a location of the IOL relative to the distal opening 12 of the nozzle 120 when the distal end 256 of the biasing element 260 contacts the proximal end 50 of the injector body 20 may vary. In some instances, the IOL may be partially ejected from the distal opening 125 when the distal end 265 of the biasing element 260 contacts the proximal end 50 of the injector body 20. For example, in some instances, approximately half of the IOL may be ejected from the distal opening 125 when the distal end 256 of the biasing element 260 contacts the proximal end 50 of the injector body 20. In other instances, the IOL may be contained wholly within the IOL injector when the distal end 256 of the biasing element 260 contacts the proximal end 50 of the injector body 20.

FIG. 21 shows a cross sectional view of the opening 170 formed at the interface 172. In some instances, the opening 170 may define a "T" shape. The plunger tip 220 is shown disposed at the opening 170 with the flexible wall portion 162 contacting a surface 214 the plunger rod 210. In some instances, the cross section of the plunger rod 210 increases towards the proximal end of the plunger rod 210. Thus, as the plunger rod 210 is advanced through the opening 170, the plunger rod 210 fills the opening as a result of the increasing cross section. Portions 173 and 175 of the opening 170 are filled by flanges 213, 215 (shown in FIG. 11).

Figure 22:
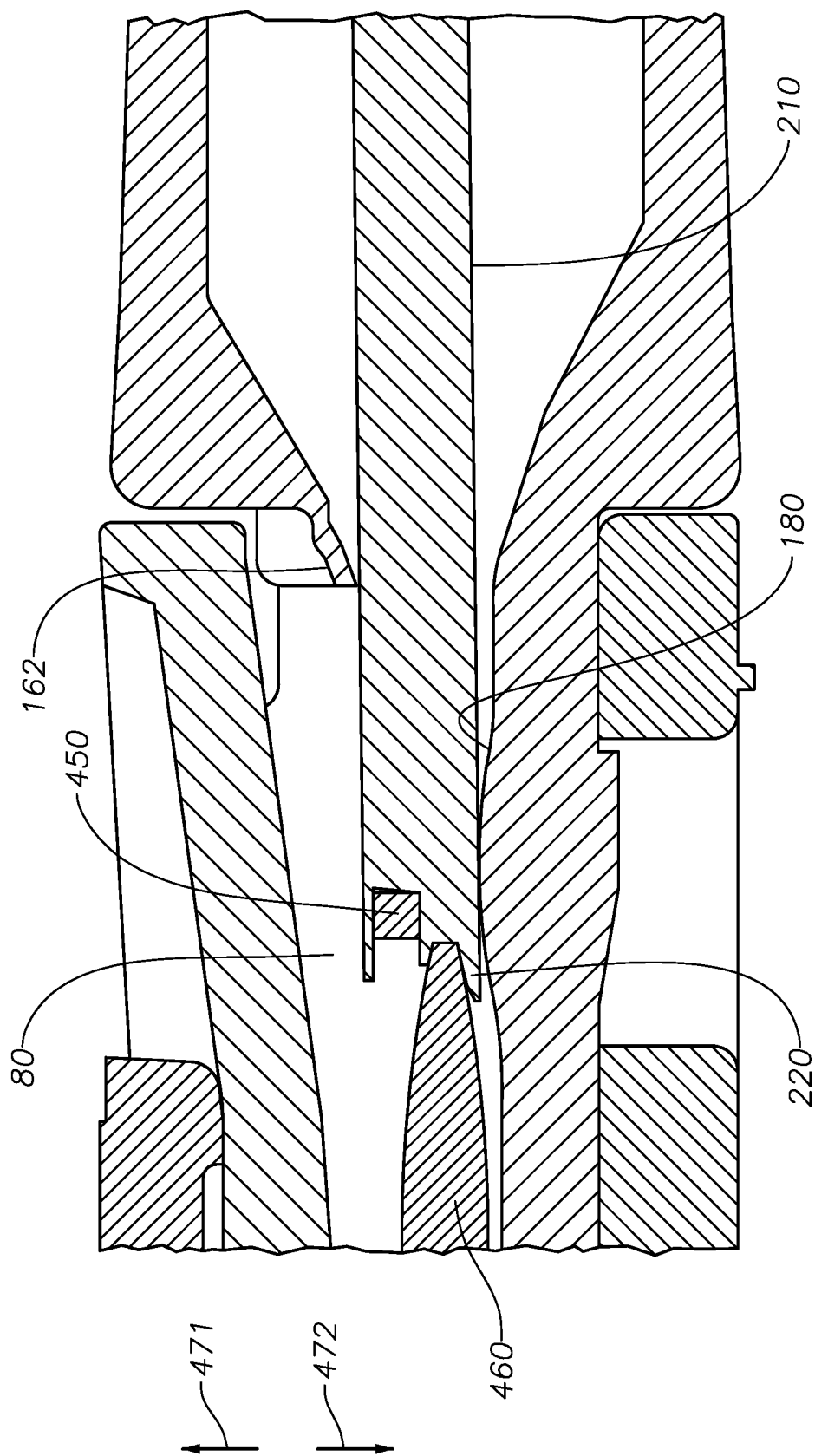
FIG. 22 is a partial cross-sectional view of an example IOL injector.

As the opening 170 is filled by the increasing cross section of the plunger rod 210 as the plunger rod 210 is advanced distally through the injector body 20, the flexible wall portion 162 is flexed in the direction of arrow 471 to permit passage of the plunger rod 210, as shown in FIG. 22. Further, as a result of the angled portion 212 of the plunger rod 210, the contoured ramp 180, and the folding of IOL 70 as it is advanced through the IOL injector 10, the plunger tip 220 is made to follow a defined path through the compartment 80, the distal end 60, and nozzle 120 uninfluenced by the flexible wall portion 162.

FIG. 22 shows the flexible wall portion 162 being flexed in the direction of 471 as the plunger rod 210 continues to advance distally through the IOL injector 10. Further, FIG. 22 also shows the plunger tip 220 engaged with IOL 70 such that trailing haptic 450 is received into the first groove 500 at a location offset from the second groove 510, and the proximal edge of the optic 460 is received into the second groove 510.

As the IOL 70 is advanced through the passage 64 of the distal end 60, the IOL 70 is folded into a reduced size to permit passage of the IOL 70 through the nozzle 120 and into the eye. During folding of the IOL 70, a resistive force on the plunger 30 is increased. Once the IOL 70 is fully folded 70, the resistive force on the plunger 30 generally reduces.

A wound may be formed in the eye. The wound may be sized to accommodate the nozzle 120 of the IOL injector 10. The nozzle 120 may be inserted into the wound. The nozzle 120 may be advanced through the wound until the flanged surface 150 of the insertion depth guard 140 abuts the exterior surface of the eye. Contact between the insertion depth guard 140 and the exterior surface of the eye limits the depth to which the nozzle 120 may be inserted into the eye, preventing unnecessary stress on the edges of the wound as well as preventing enlargement of the wound due to over insertion of the IOL injector 10. Consequently, the insertion depth guard 140 operates to reduce additional trauma to the eye and enlargement of the wound.

With the nozzle properly positioned within the eye through the wound, the user may complete delivery of the folded IOL into the eye. Referring again to FIG. 15, as advancement of the plunger 30 continues, the biasing element 260 is compressed (indicated by the dotted outline of biasing element 260). Compression of biasing element 260 increases a resistive force to advancement of the plunger 30, also referred to as plunging force. This additional resistance to advancement of the plunger 30 diminishes changes to the plunging force associated with the folding of the IOL prior to insertion into the eye. Further, in some instances, the biasing element 260 may be made to contact the injector body 120 when, or proximate to when, the IOL 70 has fully folded so that the a reduction in resistive force that may result from the IOL 70 being fully folded may be offset by the compression of the biasing element 260. This increase in resistive force provided by compression of the biasing element 260, particularly in light of a reduction that may result due to the IOL 70 being fully folded, provides improved tactile feedback to a user, such as a medical profession, during delivery of the IOL 70 into an eye. This improved tactical feedback provides the user with improved control during delivery of the IOL 70, which may prevent rapid expulsion of the IOL 70 into the eye.

As a result, the user is able to provide a smooth application of force without experiencing any sudden or rapid changes in advancement of the plunger 30. Such sudden or rapid changes may result in the IOL being rapidly expelled from an injector. Rapid expulsion of an IOL into an eye may cause damage, such as perforation of the capsular bag. Such damage may increase the time required to compete the surgical procedure and may increase the harm caused immediately and post operatively to the patient. Upon insertion of the IOL into the eye, the IOL injector 10 may be withdrawn from the eye.

Figure 23:
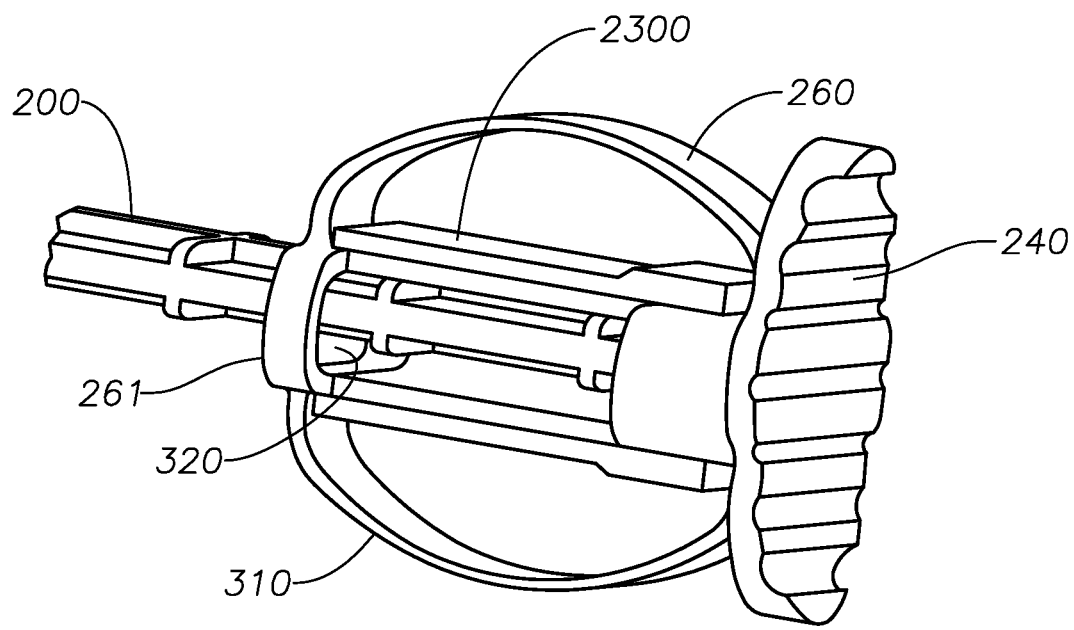
FIGS. 23-24 show an example advancement stop coupled to a plunger.
Figure 24:
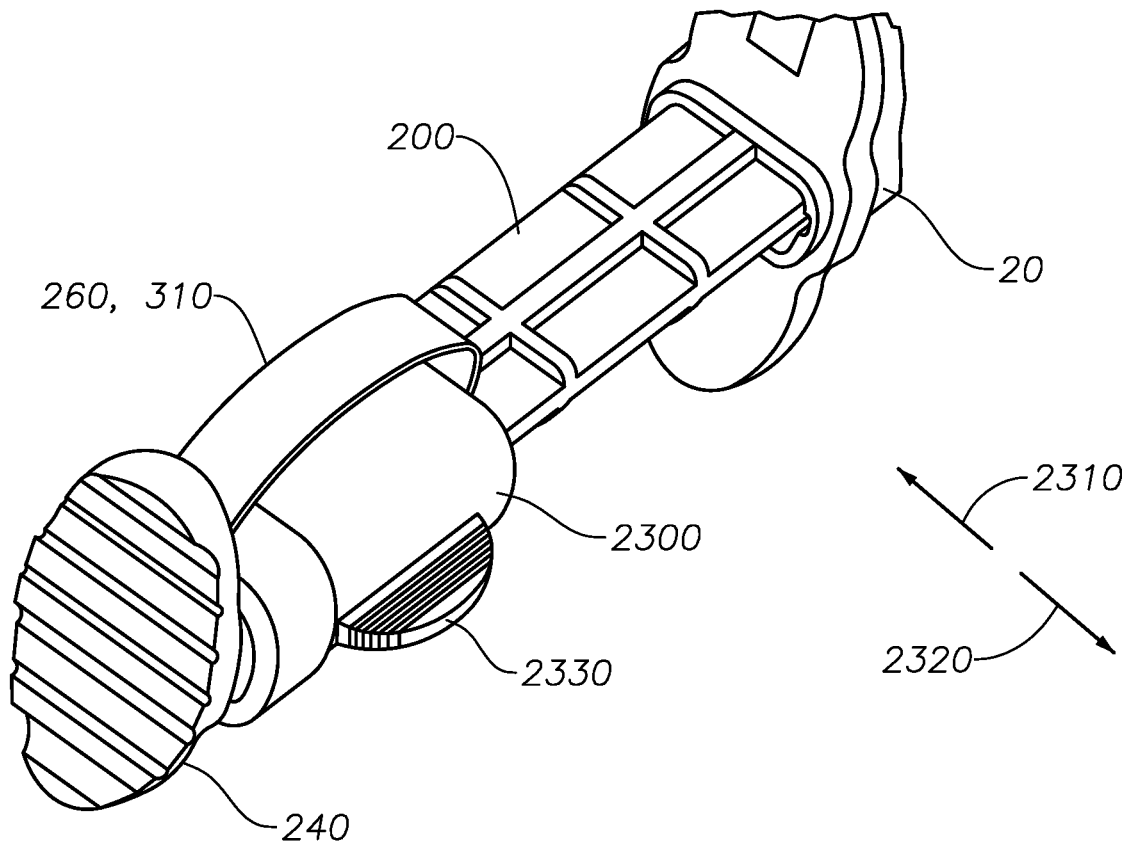

FIGS. 23-26 show example advancement stops operable to prevent actuation of biasing element 260. For example, in some instances, the example advancement stops are operable to prevent compression of the biasing element 260 and prevent advancement of the plunger 30 through the injector body 20 beyond a selected amount. Referring to FIGS. 23 and 24, an advancement stop 2300 is shown coupled to the body portion 200 of the plunger 30 between the flange 240 and the collar 261 of biasing element 260. The advancement stop 2300 may be moved into engagement with the plunger 30 laterally in the direction of arrow 2310. Similarly, the advancement stop 220 may be removed from the plunger 30 laterally displacing the advancement stop 2300 in the direction of arrow 2320. The advancement stop 2300 may be retained on the plunger 30 such as by a frictional engagement and/or a detent between one or more portions of the plunger 30 and the advancement stop 2300. A user may manipulate the advancement stop 2300 via a tab 2330 formed thereon. The advancement stop 2300 may be formed from a rigid material, such as a polymer, composite material, metal, or any other suitable material.

Inclusion of the advancement stop 2300 onto the plunger 30 prevents actuation of the biasing element 260 and further advancement of the plunger 30 through the injector body 20 when the distal end 265 of the biasing element 260 contacts the proximal end 50 of the injector body 20. Any force acting on the distal end 265 of the biasing element 260 is transmitted from the collar 261 through the advancement stop 2300 and into the flange 240. In some instances, inclusion of the advancement stop 2300 may be useful to prevent sudden ejection of an IOL from IOL injector 10 due, for example, to excessive forces applied to the IOL injector 10 by the user. In other instances, the advancement stop 2300 may be included in order to ensure that advance of the IOL ceases upon reaching a selected location within the IOL injector 10. For example, the advancement stop 2300 may prevent further advancement of the IOL once the IOL has reached the pause position. However, an advancement stop, such as the advancement stops described herein, need not be included or otherwise utilized with the IOL injector 10.

Figure 25:
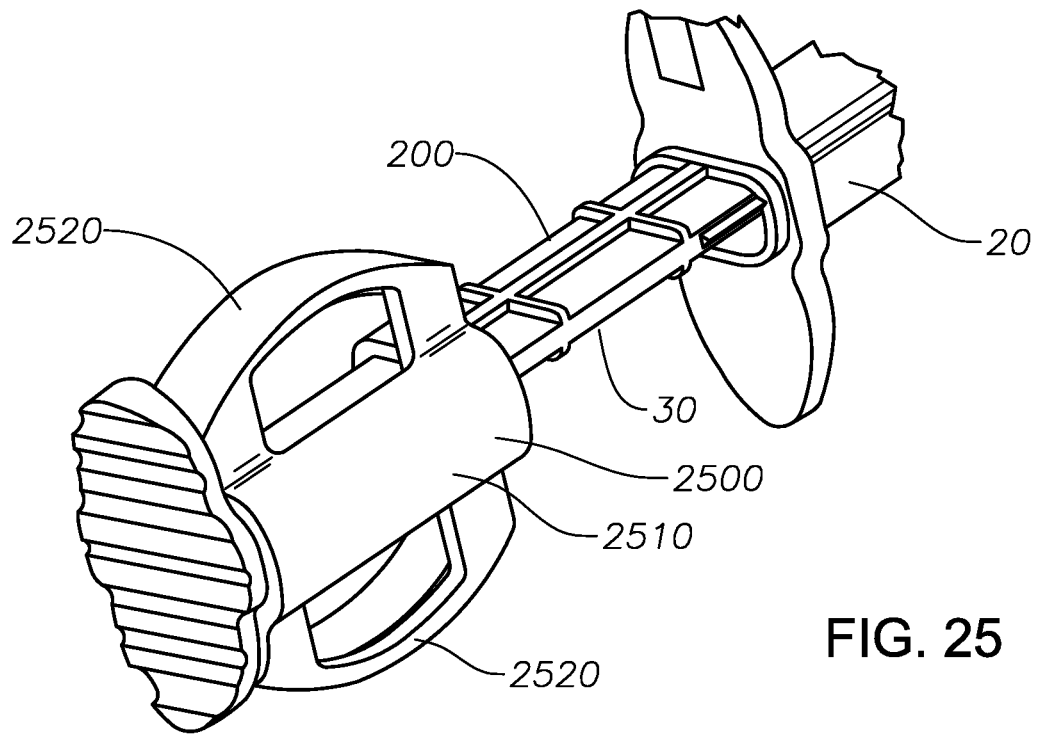
FIGS. 25-26 show another example advancement stop coupled to a plunger.
Figure 26:
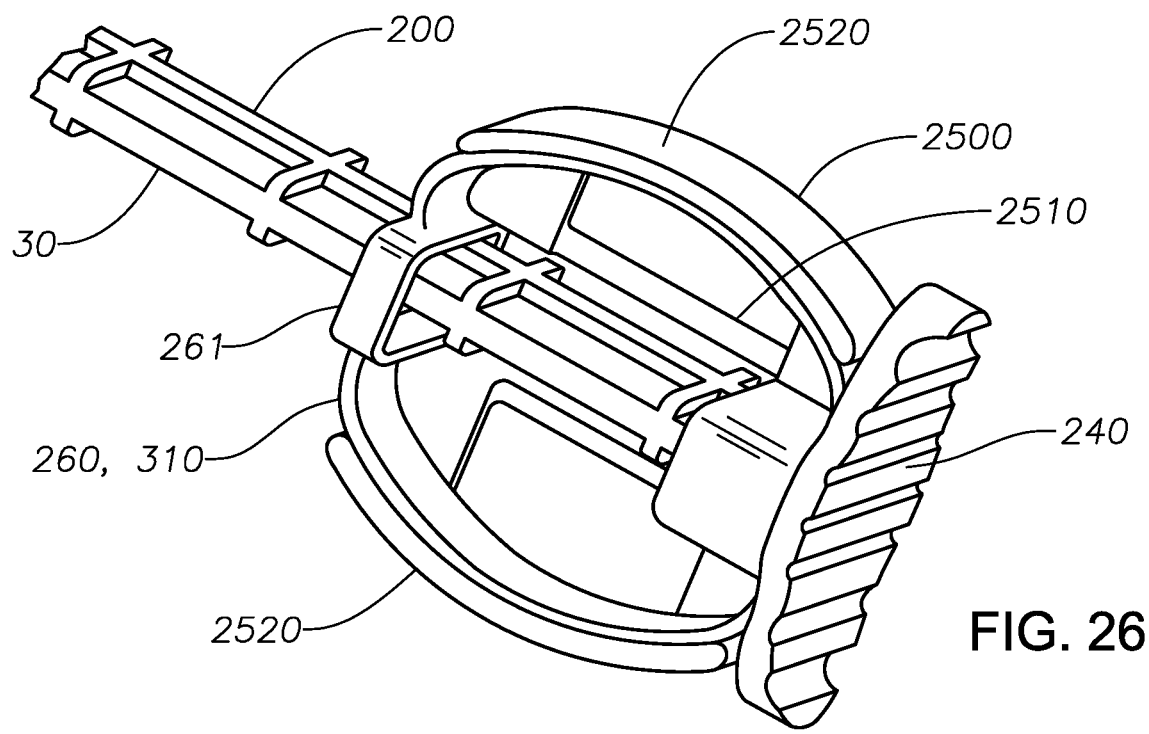

FIGS. 25-26 illustrate another example implementation of an advancement stop. Example advancement stop 2500 is shown coupled to the plunger 30. The advancement stop 2500 includes a central member 2510 with arc-shaped wings 2520 extending therefrom. The central member 2510 has an arcuate cross-section that is received onto the body portion 200 of the plunger 30. The arc shape of the wings 2520 may conform or substantially conform to the shape of the biasing element 260. The advancement stop 2500 may be retained on the plunger 30 such as by a frictional engagement and/or a detent between one or more portions of the plunger, e.g., biasing element 260 and/or body portion 200, to name a few examples, and the advancement stop 2500, e.g., surfaces of the advancement stop 2500 abutting the biasing element 260, the collar 261, and/or flange 240, to name a few examples. The advancement stop 2500 may be formed from a rigid material, such as a polymer, composite material, metal, or any other suitable material.

Advancement stop 2500 may operate similarly to the advancement stop 2300. When coupled to the plunger 30, the advancement stop 2500 limits an amount the plunger 30 may be displaced within the injector body 20. In some instances, when the plunger 30 has been displaced within the injector body 20 by the selected amount, a distal end of the central member 2510 contacts the proximal end 50 of the injector body 20. The central member 2510 transmits any force to the flange 240, thereby preventing actuation of the biasing element 260. In other instances, the collar 261 may contact the proximal end 50 of the injector body 20. However, the close engagement between the biasing element 260 and the conforming wings 2520 prevents outward flexure of the biasing element 260, thereby preventing actuation of the biasing element 260.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure.

What is claimed is:

1. An intraocular lens injector comprising:
   an injector body comprising:
      a bore defined by an interior wall;
      an insertion depth guard disposed at a distal end of the injector body, the insertion depth guard comprising a concave curved flanged surface with a curvature that corresponds to an eye; and
      a nozzle extending distally beyond the insertion depth guard and fixed to the insertion depth guard; and
   a plunger slideable in the bore;
   wherein the concave curved flanged surface has radii of curvature extending from a center displaced beyond an end of the nozzle distally.

2. The intraocular lens injector of claim 1, wherein the concave curved flanged surface is a spherical surface.

3. The intraocular lens injector of claim 1, wherein the plunger comprises:
   a body portion; and
   a biasing element disposed adjacent to a proximal end of the body portion, the biasing element deformable upon engagement with the injector body to produce a force resistive to further advancement of the plunger through the bore.

4. The intraocular lens injector of claim 3, wherein the biasing element comprises a channel, and wherein the body portion of the plunger extends through the channel.

5. The intraocular lens injector of claim 1, wherein the injector body further comprises:
   a tab formed at a proximal end thereof;
   a groove extending through the tab; and
   an aperture aligned with the groove.

6. The intraocular lens injector of claim 5 further comprising a plunger stop comprising a protrusion, wherein the plunger stop is removably received in the groove such that the protrusion extends through the aperture and into a slot formed in the plunger.

7. The intraocular lens injector of claim 6, wherein the plunger comprises a cantilevered member, wherein the bore comprises a shoulder, and the aperture formed in the injector body aligns with the slot formed in the plunger when the cantilevered member engages the shoulder.

8. The intraocular lens injector of claim 1, wherein the plunger comprises a cantilevered member and wherein the cantilevered member deflectively engages the interior wall of the bore as the plunger is advanced through the bore.

9. The intraocular lens injector of claim 1 further comprising an advancement stop removably coupled to the plunger, the advancement stop adapted to limit an amount by which the plunger is permitted to advance through the bore.

10. The intraocular lens injector of claim 1, wherein the nozzle and the insertion depth guard are made of a single piece of material.

11. An intraocular lens injector comprising:
an injector body comprising:
 a bore defined by an interior wall;
 a nozzle formed at a distal end of the injector body; and
a plunger slideable in the bore, the plunger comprising a plunger tip that includes:
 a first groove that extends longitudinally from the plunger tip and along at least a portion of a first lateral side of the plunger without extending along a second lateral side of the plunger opposite the first lateral side, the first lateral side and the second lateral side extending generally along a longitudinal axis defined by the plunger, the first groove forming a first shelf, the first shelf generally parallel with a bottom-most surface of the plunger and open to a space adjacent to a top-most surface of the plunger, and
 a second groove extending laterally from the first lateral side to the second lateral side.

12. The intraocular lens injector of claim 11, wherein the second groove is formed at a first end of the first groove.

13. The intraocular lens injector of claim 12, wherein a second end of the first groove opposite the first end is configured to capture a trailing haptic of an intraocular lens disposed in the injector body, and wherein the second groove is adapted to capture a proximal end of an optic of the intraocular lens.

14. The intraocular lens injector of claim 11, wherein the plunger comprises a plunger rod, and wherein at least a portion of the plunger rod is angularly offset from a longitudinal axis of the plunger rod.

15. The intraocular lens injector of claim 11, wherein the injector body further comprises an insertion depth guard disposed at a distal end of the injector body and wherein the insertion depth guard comprises a flanged surface.

16. The intraocular lens injector of claim 15, wherein a cross-sectional dimension of the insertion depth guard is larger than a cross-sectional dimension of the nozzle.

17. The intraocular lens injector of claim 15, wherein the flanged surface is a curved surface.

18. The intraocular lens injector of claim 11, wherein the plunger comprises:
 a biasing element disposed adjacent to a proximal end of the plunger, the biasing element deformable upon engagement with the injector body to produce a force resistive to further advancement of the plunger through the bore.

19. The intraocular lens injector of claim 18, wherein the biasing element comprises a channel, and wherein a body portion of the plunger extends through the channel.

20. The intraocular lens injector of claim 11 further comprising an advancement stop removably coupled to the plunger, the advancement stop adapted to limit an amount by which the plunger is permitted to advance through the bore.

* * * * *